US009980976B2

(12) United States Patent
Budunova et al.

(10) Patent No.: US 9,980,976 B2
(45) Date of Patent: May 29, 2018

(54) USE OF REDD1 INHIBITORS TO DISSOCIATE THERAPEUTIC AND ADVERSE ATROPHOGENIC EFFECTS OF GLUCOCORTICOID RECEPTOR AGONISTS

(71) Applicant: Northwestern University, Evanston, IL (US)

(72) Inventors: Irina Budunova, Chicago, IL (US); Gleb Baida, Chicago, IL (US); Joel Dudley, Rye, NY (US)

(73) Assignee: Northwestern University, Evanston, IL (US)

( * ) Notice: Subject to any disclaimer, the term of this patent is extended or adjusted under 35 U.S.C. 154(b) by 0 days. days.

(21) Appl. No.: 15/046,075

(22) Filed: Feb. 17, 2016

(65) Prior Publication Data
US 2016/0235763 A1  Aug. 18, 2016

Related U.S. Application Data

(60) Provisional application No. 62/117,248, filed on Feb. 17, 2015.

(51) Int. Cl.
| *A61K 31/56* | (2006.01) |
| *A61K 31/436* | (2006.01) |
| *A61K 45/06* | (2006.01) |
| *A61K 31/407* | (2006.01) |
| *A61K 31/4164* | (2006.01) |
| *A61K 31/429* | (2006.01) |
| *A61K 31/498* | (2006.01) |
| *A61K 31/542* | (2006.01) |
| *A61K 31/573* | (2006.01) |
| *A61K 31/58* | (2006.01) |
| *A61K 31/7076* | (2006.01) |

(52) U.S. Cl.
CPC ............ *A61K 31/56* (2013.01); *A61K 31/407* (2013.01); *A61K 31/4164* (2013.01); *A61K 31/429* (2013.01); *A61K 31/436* (2013.01); *A61K 31/498* (2013.01); *A61K 31/542* (2013.01); *A61K 31/573* (2013.01); *A61K 31/58* (2013.01); *A61K 31/7076* (2013.01); *A61K 45/06* (2013.01)

(58) Field of Classification Search
CPC ............ A61K 31/407; A61K 31/4164; A61K 31/429; A61K 31/436; A61K 31/498; A61K 31/542; A61K 31/56; A61K 31/573; A61K 31/58; A61K 31/7076; A61K 45/06
USPC ........................................................ 514/171
See application file for complete search history.

(56) References Cited

U.S. PATENT DOCUMENTS 8,258,153 B2 * 9/2012 Chappell .............. A61K 31/222
                                                    514/179
8,716,322 B2 * 5/2014 Zhou ...................... A61K 38/55
                                                    514/171

OTHER PUBLICATIONS

Schäcke H, Zollner TM, Döcke WD, Rehwinkel H, Jaroch S, Skuballa W, Neuhaus R, May E, Zügel U, Asadullah K. Characterization of ZK 245186, a novel, selective glucocorticoid receptor agonist for the topical treatment of inflammatory skin diseases. Br J Pharmacol. 2009;158:1088-1103.
Schoepe S. Schäcke H, May E, Asadullah K. Glucocorticoid therapy-induced skin atrophy. Exp Dermatol. 2006;15:406-420.
Schoepe S, Schäcke H, Bernd A, Zöller N, Asadullah K. Identification of novel in vitro test systems for the determination of glucocorticoid receptor ligand-induced skin atrophy. Skin Pharmacol Physiol. 2010;23:139-151.
Sheehan DC, Hrapchak B. Theory and Practice of Histotechnology. St Louis, MO, USA: The C.V. Mosby Company; 1980.
Shimizu N, Yoshikawa N, Ito N, Maruyama T, Suzuki Y, Takeda S, Nakae J, Tagata Y, Nishitani S, Takehana K, et al. Crosstalk between glucocorticoid receptor and nutritional sensor mTOR in skeletal muscle. Cell Metab. 2011;13:170-182.
Shoshani T, Faerman A, Mett I, Zelin E, Tenne T, Gorodin S, Moshel Y, Elbaz S, Budanov A, Chajut A, et al. Identification of a novel hypoxia-inducible factor 1-responsive gene, RTP801, involved in apoptosis. Mol Cell Biol. 2002;22:2283-2293.
Smyth GK. Limma: linear models for microarray data. In: Gentleman R, Carey V, Dudoit S, Irizarry R, Huber W, et al., editors. Bioinformatics and Computational Biology Solutions using R and Bioconductor. New York: Springer; 2005. pp. 397-420.
Sofer A, Lei K, Johannessen CM, Ellisen LW. Regulation of mTOR and cell growth in response to energy stress by REDD1. Mol Cell Biol. 2005;25:5834-5845.
Taheri A, Cantrell J, Feldman SR. Tachyphylaxis to topical glucocorticoids; what is the evidence? Dermatol Online J. 2013;9:18954-18961.
Vandevyver S, Dejager L, Libert C. On the trail of the glucocorticoid receptor: into the nucleus and back. Traffic. 2012;13:364-374.
Wang H, Kubica N, Ellisen LW, Jefferson LS, Kimball SR. Dexamethasone represses signaling through the mammalian target of rapamycin in muscle cells by enhancing expression of REDD1. J Biol Chem. 2006;281:39128-39134.

(Continued)

*Primary Examiner* — My-Chau T. Tran
(74) *Attorney, Agent, or Firm* — Andrus Intellectual Property Law, LLP

(57) ABSTRACT

Disclosed are methods and pharmaceutical compositions for treating diseases, disorders, and conditions associated with glucocorticoid receptor (GR) expression and activity. The disclosed methods typically include administering to a patient in need thereof a glucocorticoid receptor (GR) agonist and administering to the patient in need thereof a REDD1 inhibitor that inhibits expression or activity of REDD1, wherein the REDD1 inhibitor is administered before, concurrently with, or after the GR agonist is administered.

18 Claims, 17 Drawing Sheets

(56) References Cited

OTHER PUBLICATIONS

Woodbury R, Kligman AM. The hairless mouse model for assaying the atrophogenicity of topical corticosteroids. Acta Derm Venereol. 1992;72:403-406.
Wu W, Chaudhuri S, Brickley DR, Pang D, Karrison T, Conzen SD. Microarray analysis reveals glucocorticoid-regulated survival genes that are associated with inhibition of apoptosis in breast epithelial cells. Cancer Res. 2004;64:1757-1764.
Yemelyanov A, Czwornog J, Chebotaev D, Karseladze A, Kulevitch E, Yang X, Budunova I. Tumor suppressor activity of glucocorticoid receptor in the prostate. Oncogene. 2007;26:1885-1896.
Yemelyanov A, Czwornog J, Gera L, Joshi S, Chatterton RT, Jr, Budunova I. Novel steroid receptor phyto-modulator compound A inhibits growth and survival of prostate cancer cells. Cancer Res. 2008;68:4763-4773.
Yoshida T, Mett I, Bhunia AK, Bowman J, Perez M, Zhang L, Gandjeva A, Zhen L, Chukwuek U, Mao T, et al. Rtp801, a suppressor of mTOR signaling, is an essential mediator of cigarette smoke-induced pulmonary injury and emphysema. Nat Med. 2010;16:767-773.
Zheng PS, Lavker RM, Lehmann P, Kligma AM. Morphologic investigations on the rebound phenomenon after corticosteroid-induced atrophy in human skin. J Invest Dermatol. 1984;82:345-352.
Zufferey R, Dull T, Mandel RJ, Bukovsky A, Quiroz D, Naldini L, Trono D. Self-inactivating lentivirus vector for safe and efficient in vivo gene delivery. J Virol. 1998;72:9873-9880.
Adcock IM. Glucocorticoid-regulated transcription factors. Pulm Pharmacol Ther. 2001;14:211-219.
Beswick EJ, Reyes VE. CD74 in antigen presentation, inflammation, and cancer. World J Gastroenterol. 2009;15:2855-2861.
Boukamp P, Petrussevska RT, Breitkreutz D, Homung J, Markham A, Fusenig NE. Normal keratinization in a spontaneously immortalized aneuploid human keratinocyte cell line. J Cell Biol. 1988;106:761-771.
Brafman A, Mett I, Shafir M, Gottlieb H, Darnari G, Gozlan-Kelner S, Vishnevskia-Dai V, Skaliter R, Einat P, Faerman A, et al. Inhibition of oxygen-induced retinopathy in RTP801-deficient mice. Invest Ophthalmol Vis Sci. 2004;45:3796-3805.
Brugarolas J, Lei K, Hurley RL, Manning BD, Reiling JH, Hafen E, Witters LA, Ellisen LW, Kaelin WG., Jr Regulation of mTOR function in response to hypoxia by REDD1 and the TSC1/TSC2 tumor suppressor complex. Genes Dev. 2004;18:2893-2904.
Chebotaev D, Yemelyanov A, Budunova I. The mechanisms of tumor suppressor effect of glucocorticoid receptor in skin. Mol Carcinog. 2007a;46:732-740.
Chebotaev D. Yemelyanov A, Zhu L, Lavker RM, Budunova I. The tumor suppressor effect of the glucocorticoid receptor in skin is mediated via its effect on follicular epithelial stem cells. Oncogene. 2007b;26:3060-3068.
Chebotaev DV, Yemelyanov A, Lavker RM, Budunova I. Epithelial cells in the hair follicle bulge do not contribute to epidermal regeneration after glucocorticoid-induced cutaneous atrophy. J Invest Dermatol. 2007c;127:2749-2758.
Checkley LA, Rho O, Moore T, Hursting S. DiGiovanni J. Rapamycin is a potent inhibitor of skin tumor promotion by 12-O-tetradecanoylphorbol-13-acetate. Cancer Prev Res. 2011;4;1011-1020.
Clark AR, Martin JR, Tchen CR. Role of dual specificity phosphatases in biological responses to glucocorticoids. J Biol Chem. 2008;283:25765-25769.
Corominas-Faja B, Cuff S, Oliveras-Ferraros C, Cuyàs E, López-Bonet E, Lupu R, Alarcón T, Vellon L, Iglesias JM, Leis O, et al. Nuclear reprogramming of luminal-like breast cancer cells generates Sox2-overexpressing cancer stem-like cellular states harboring transcriptional activation of the mTOR pathway. Cell Cycle. 2013;12:3109-3124.
De Bosscher K, Vanden Berghe W, Haegeman G. The interplay between the glucocorticoid receptor and nuclear factor-kappaB or activator protein-1: molecular mechanisms for gene repression. Endocr Rev. 2003;24:488-522.
De Bosscher K, Haegeman G, Elewaut D. Targeting inflammation using selective glucocorticoid receptor modulators. Curr Opin Pharmacol. 2010;10:497-504.
De Guzman Strong C, Conlan S, Deming CB, Cheng J, Sears KE, Segre JA. A milieu of regulatory elements in the epidermal differentiation complex syntenic block: implications for atopic dermatitis and psoriasis. Hum Mol Genet. 2010;19:1453-1460.
DeYoung MP, Horak P, Sofer A, Sgroi D, Ellisen LW. Hypoxia regulates TSC1/2-mTOR signaling and tumor suppression through REDD1-mediated 14-3-3 shuffling. Genes Dev. 2008;22:239-251.
Driskell RR, Lichtenberger BM, Hoste E, Kretzschmar K, Simons BD, Charalambous M, Ferron SR, Herault Y, Pavlovic G, Ferguson-Smith AC, et al. Distinct fibroblast lineages determine dermal architecture in skin development and repair. Nature. 2013;504:277-281.
Dudley JT, Sirota M, Shenoy M, Pai RK, Roedder S, Chiang AP, Morgan AA, Sarwal MM, Pasricha PJ, Butte AJ. Computational repositioning of the anticonvulsant topiramate for inflammatory bowel disease. Sci Transl Med. 2011;3:96-103.
Ellisen LW, Ramsayer KD, Johannessen CM, Yang A, Beppu H, Minda K, Oliner JD, McKeon F, Haber DA. REDD1, a developmentally regulated transcriptional target of p63 and p53, links p63 to regulation of reactive oxygen species. Mol Cell. 2002;10:995-1005.
Ellisen LW. Growth control under stress: mTOR regulation through the REDD1-TSC pathway. Cell Cycle. 2005;4:1500-1502.
Engreitz JM, Morgan AA, Dudley JT, Chen R, Thalhoo R, Altman RB, Butte AJ. Content-based microarray search using differential expression profiles. BMC Bioinformatics. 2010;11:603-614.
Getsios S, Simpson CL, Kojima S, Harmon R, Sheu LJ, Dusek RL, Cornwell M, Green KJ. Desmoglein 1-dependent suppression of EGFR signaling promotes epidermal differentiation and morphogenesis. J Cell Biol. 2009;185:1243-1258.
Guillou H, Zadravec D, Marlin PG, Jacobsson A. The key roles of elongases and desaturases in mammalian fatty acid metabolism: insights from transgenic mice. Prog Lipid Res. 2010;49:186-199.
Henneicke H, Gasparini SJ, Brennan-Speranza TC, Zhou H, Seibel MJ. Glucocorticoids and bone: local effects and systemic implications. Trends Endocrinol Metab. 2014;25:197-211.
Huang DW, Sherman BT, Lempicki RA. Bioinformatics enrichment tools: paths toward the comprehensive functional analysis of large gene lists. Nucleic Acids Res. 2009b;37:1-13.
Imagawa K, Ohkuma S. A case of fat injection for treating subcutaneous atrophy caused by local administration of corticosteroid. Tokai J Exp Clin Med. 2010;35:66-69.
Jablonska S, Groniowska M, Dabroswki J. Comparative evaluation of skin atrophy in man induced by topical corticoids. Br J Dermatol. 1979;100:193-206.
de Jonge HJ, Fehrmann RS, de Bont ES, Hofstra RM, Gerbens F, Kamps WA, de Vries EG, van der Zee AG, te Meerman GJ, ter Elst A. Evidence based selection of housekeeping genes. PLoS One. 2007;2:e898.
Kamocki K, Van Demark M, Fisher A, Rush NI, Presson RG, Hubbard W, Berdyshev EV, Adamsky S, Feinstein E, Gandjeva A, et al. RTP801 is required for ceramide-induced cell-specific death in the murine lung. Am J Respir Cell Mol Biol. 2013;48:87-93.
Katiyar S. Liu E, Knutzen CA, Lang ES, Lombardo CR, Sankar S, Toth JI, Petroski MD, Ronai Z, Chiang GG. REDD1, an inhibitor of mTOR signalling, is regulated by the CUL4A-DDB1 ubiquitin ligase. EMBO Rep. 2009;10:866-872.
Klionsky DJ, Abdalla FC, Abeliovich H, Abraham RT, Acevedo-Arozena A, Adeli K, Agholme L, Agnello M, Agostinis P, Aguirre-Ghiso JA, et al. Guidelines for the use and interpretation of assays for monitoring autophagy. Autophagy. 2012,8:445-544.
Larsen L, Röpke C. Suppressors of cytokine signalling: SOCS. APMIS. 2002;110:833-844.
Lehmann P, Zheng P. Lavker RM, Kligman AM. Corticosteroid atrophy in human skin. A study by light, scanning, and transmission electron microscopy. J Invest Dermatol. 1983;81:169-176.
Li L, Lou Z, Wang L. The role of FKBP5 in cancer aetiology and chemoresistance. Br J Cancer. 2011;104:19-23.

(56) References Cited

OTHER PUBLICATIONS

Li XH, Ha CT, Fu D, Xiao M. REDD1 protects osteoblast cells from gamma radiation-induced premature senescence. PLoS One. 2012;7:e36604.

Lin L, Qian Y, Shi X, Chen Y. Induction of a cell stress response gene RTP801 by DNA damaging agent methyl methanesulfonate through CCAAT/enhancer binding protein. Biochemistry. 2005;44:3909-3914.

Lubach D, Kietzmann M. Investigation of the skin thinning effect of prednicarbate and other corticoids in mouse skin. Skin Pharmacol. 1988;1:200-206.

Mata MA, Satterly N. Versteeg GA, Frantz D, Wei S, Williams N, Schmolke M, Peña-Llopis S, Brugarolas J, Forst CV, at al. Chemical inhibition of RNA viruses reveals REDD1 as a host defense factor. Nat Chem Biol. 2011;7:712-719.

Molitoris JK, McColl KS, Swerdlow S, Matsuyama M, Lam M, Finkel TH, Matsuyama S, Distelhorst CW. Glucocorticoid elevation of dexamethasone-induced gene 2 (Dig2/RTP801/REDD1) protein mediates autophagy in lymphocytes. J Biol Chem. 2011;286:30181-30189.

Necela BM, Cidlowski JA. Mechanisms of glucocorticoid receptor action in noninflammatory and inflammatory cells. Proc Am Thorac Soc. 2004;1:239-246.

Nixon M, Andrew R, Chapman KE. It takes two to tango: dimerisation of glucocorticoid receptor and its anti-inflammatory functions. Steroids. 2013;78:59-68.

Pan J, Ju D, Wang Q, Zhang M, Xia D, Zhang L, Yu H, Cao X. Dexamethasone inhibits the antigen presentation of dendritic cells in MHC class II pathway. Immunol Lett. 2001;76:153-161.

Park KK, Ko DH, You Z, Heiman AS, Lee HJ. Synthesis and pharmacological evaluations of new steroidal anti-inflammatory antedrugs: 9alpha-Fluoro-11beta, 17alpha, 21-trihydroxy-3,20-dioxopregna-1,4-diene-16alpha-carboxylate (FP16CM) and its derivatives. Steroids. 2006;71:83-89.

Park KW, Halperin DS, Tontonoz P. Before they were fat: adipocyte progenitors. Cell Metab. 2008;8:454-457.

Pineau P. Volinia S, McJunkin K, Marchio A, Battiston Terris CB, Mazzaferro V. Lowe SW, Croce CM, Dejean A. miR-221 overexpression contributes to liver tumorigenesis. Proc Natl Acad Sci USA. 2010;107:264-269.

Ratman D, Vanden Berghe W, Dejager L, Libert C, Tavernier J, Beck IM, De Bosscher K. How glucocorticoid receptors modulate the activity of other transcription factors: a scope beyond tethering. Mol Cell Endocrinol. 2013;380:41-54.

Regazzetti C, Dumas K, Le Y, Marchand-Brustel F, Peraldi P, Tanti JF, Giorgetti-Peraldi S. Regulated in Development and DNA Damage Responses-1 (REDD1) protein contributes to insulin signaling pathway in adipocytes. PLoS ONE. 2012;7:e52154.

Schäcke H, Schottelius A, Döcke WD, Strehlke P, Jaroch S, Schmees N, Rehwinkel H, Hennekes H, Asadullah K. Dissociation of transactivation from transrepression by a selective glucocorticoid receptor agonist leads to separation of therapeutic effects from side effects. Proc Natl Acad Sci USA. 2004;101:227-232.

Schäcke H, Rehwinkel H, Asadullah K. Cato AC. Insight into the molecular mechanisms of glucocorticoid receptor action promotes identification of novel ligands with an improved therapeutic index. Exp Dermatol. 2006;15:565-573.

Baida G, Bhalla P, Yuen K, Guo S, Lavker RM, Budunova I. mTOR inhibitor REDD1 protects CD34+ follicular epithelial stem cells and prevents development of steroid-induced cutaneous atrophy. J Invest Dermatol. 2013;133:S243-S246.

Huang DW, Sherman BT, Lempicki RA. Systematic and integrative analysis of large gene lists using DAVID Bioinformatics Resources. Nat Protoc. 2009a;4:44-57.

* cited by examiner

USE OF REDD1 INHIBITORS TO DISSOCIATE THERAPEUTIC AND ADVERSE ATROPHOGENIC EFFECTS OF GLUCOCORTICOID RECEPTOR AGONISTS

CROSS-REFERENCE TO RELATED PATENT APPLICATIONS

This application claims the benefit of priority to U.S. Provisional Patent Application No. 62/117,248, filed on Feb. 17, 2015, the content of which is incorporated herein by reference in its entirety.

STATEMENT REGARDING FEDERALLY SPONSORED RESEARCH OR DEVELOPMENT

This invention was made with government support under R01 CA118890 and R01 GM112945 awarded by the National Institutes of Health. The government has certain rights in the invention.

BACKGROUND

The field of the invention relates to methods for treating diseases and disorders associated with glucocorticoid receptor (GR) activity. In particular, the field of the invention relates to methods for treating diseases and disorders associated with GR activity by administering a GR agonist and an inhibitor of the regulated in development and DNA damage response protein 1 (REDD1).

Glucocorticoid hormones are a mainstay of therapy of numerous hyperproliferative and inflammatory diseases including asthma, arthritis, psoriasis, dermatitis and others. They are also major component of chemotherapy of numerous blood cancers including acute childhood leukemia and multiple myeloma.

The biological effects of glucocorticoids are mediated by the glucocorticoid receptor (GR), which functions as a ligand-specific transcription factor. In non-activated cells, the GR resides in the cytoplasm in a complex with chaperone proteins. Upon activation by a GR agonist, the GRs dissociate from the chaperones, form homo-dimers, and enter the nucleus where they interact with the regulatory sequences in gene promoters. The GR regulates gene expression via (i) DNA-dependent transactivation that requires GR homodimerization and binding of the GR homodimer to gene promoters, which is referred to as "GR-transactivation," and (ii) DNA-independent transrepression mediated via negative interaction between the GR monomer and other transcription factors, which is referred to as "GR-transrepression." GR agonists are administered therapeutically for their anti-inflammatory and anti-proliferative effects, which are mediated via GR-transrepression. However, many negative metabolic side effects of GR agonist are mediated by GR-transactivation including glucocorticoid-induced skin atrophy, otherwise referred to as the glucocorticoid atrophogenic effect. As such, new therapies that utilize GR agonists and dissociate the therapeutic effects from the atrophogenic effects are desirable.

SUMMARY

The present inventors have discovered that glucocorticoids significantly increase the expression of REDD1 (regulated in development and DNA damage response 1), a stress-inducible inhibitor of mTOR, in human and mouse skin. The inventors also determined that REDD1 plays a critical role in the activation of glucocorticoid-responsive genes by the glucocorticoid receptor (GR). Most importantly, REDD1 knockout (KO) animals appear to be resistant to glucocorticoid-induced skin atrophy, and the inventors identified the protection of epidermal stem cells as an underlying mechanism for the anti-atrophogenic effect of REDD1. In contrast, REDD1 KO mice were as sensitive as wild-type mice to the anti-inflammatory effects of glucocorticoids. This suggests that REDD1 dissociates the beneficial therapeutic effects from adverse atrophogenic effects of glucocorticoids in skin. Using bioinformatics, the inventors compared their array of data with thousands of publicly available DNA arrays, and identified a shared REDD1-dependent molecular mechanism underlying steroid-induced atrophy in epidermis, subcutaneous fat, and muscle. The inventors also identified potential REDD1 inhibitors among FDA-approved compounds. Collectively, the inventors' findings: a) introduce the concept of innovative safer therapies with glucocorticoids using REDD1 inhibitors to reduce/alleviate glucocorticoid-induced skin atrophy and glucocorticoid atrophogenic effects in other tissues; and b) identify REDD1 inhibitors that may be used for such GR-targeted therapies.

Accordingly, disclosed are methods and pharmaceutical compositions for treating or preventing diseases, disorders, and conditions associated with glucocorticoid receptor (GR) activities. The diseases, disorders and conditions treated or prevented by the methods disclosed herein typically are responsive to administration of a GR agonist, such as known glucocorticoids.

In some embodiments, the disclosed methods include administering to a patient in need thereof a GR agonist and administering to the patient in need thereof an inhibitor of the regulated in development and DNA damage response protein 1 (REDD1). The REDD1 inhibitor may inhibit expression or activity of REDD1. The REDD1 inhibitor may be administered before, concurrently with, or after the GR agonist is administered.

In some embodiments, the disclosed methods include administering an effective amount of a REDD1 inhibitor to a patient exhibiting GR agonist induced atrophogenic effects and/or to a patient at risk for developing GR agonist induced atrophogenic effects. Atrophogenic effects may include but are not limited to epidermal atropy, epidermal hypoplasia, epidermal thinning, and/or depletion of the interfollicular basal keratinocyte population.

Typically, the patient is administered an effective amount of the GR agonist. For example, the effective amount of the GR agonist may result in transrepression of responsive genes in cells of the patient (e.g., in epithelial or lymphoid cells). The effective amount of the GR agonist may result in an anti-inflammatory effect and/or an anti-proliferative effect.

The patient may be administered an effective amount of the REDD1 inhibitor before, concurrently with, or after the effective amount of the GR agonist. In some embodiments, the patient has previously been administered a GR agonist and subsequently is administered the REDD1 inhibitor. In other embodiments, the patient has not previously been administered a GR agonist, prior to the patient being administered the REDD1 inhibitor. The effective amount of the REDD1 inhibitor may result in an anti-antrophogenic effect.

Suitable patients for the methods disclosed herein may include a patient having or at risk for developing an inflammatory disease or disorder, which may include but is not limited to asthma, arthritis, psoriasis, and dermatitis. Suitable patients for the methods disclosed herein also may include a patient having or at risk for developing cancer, which may include but is not limited to leukemia and myeloma.

Suitable REDD1 inhibitors for use in the methods disclosed herein may include but are not limited to levamisole, clofazimine, metronidazole, bucladesine, tenoxicam, physostigmine, rapamycin, and pharmaceutically acceptable salts thereof. The REDD1 inhibitor preferably is administered at a dose that counteracts the negative side effects of treatment with a GR agonist. In some embodiments, the REDD1 inhibitor preferably is administered at a dose that counteracts one or more of epidermal atrophy, epidermal hypoplasia, epidermal thinning, and depletion of the interfollicular basal keratinocyte population, preferably by at least 10%, 20%, 30%, 40%, 50%, 60%, 70%, 80%, 90%, or 100%, relative to an untreated control.

Suitable GR agonists for use in the methods disclosed herein may include but are not limited to cortisone, cortisol (hydrocortisone), corticosterone, deoxycorticosterone acetate (DOCA), fluticasone propionate, fluocinolone acetonide (FA), GSK9027, prednisone, prednisolone, methylpredinosolone, dexamethasone, betamethasone, triamcinolone, beclometasone, fludrocortisone acetate, mometasone furoate, clobetasol propionate, isoflupredone, fludrocortisone, diflorasone, prednicarbate, aclometasone, halcinonide, fludroxycortide, fluorometholone, budesonide, flumetasone, desoxycortone, medrysone, rimexonlone, flunisolide, and pharmaceutically acceptable salts thereof. In the disclosed methods, the GR agonist typically is administered to a patient in need thereof at a dose that treats or prevents an inflammatory disease or disorder or cell proliferation (e.g., cell proliferation of cancer cells) in the patient.

Also contemplated herein are pharmaceutical compositions and kits. The compositions and kits may include a combination of a REDD1 inhibitor and a GR agonist as contemplated herein.

DETAILED DESCRIPTION

Figure 1:
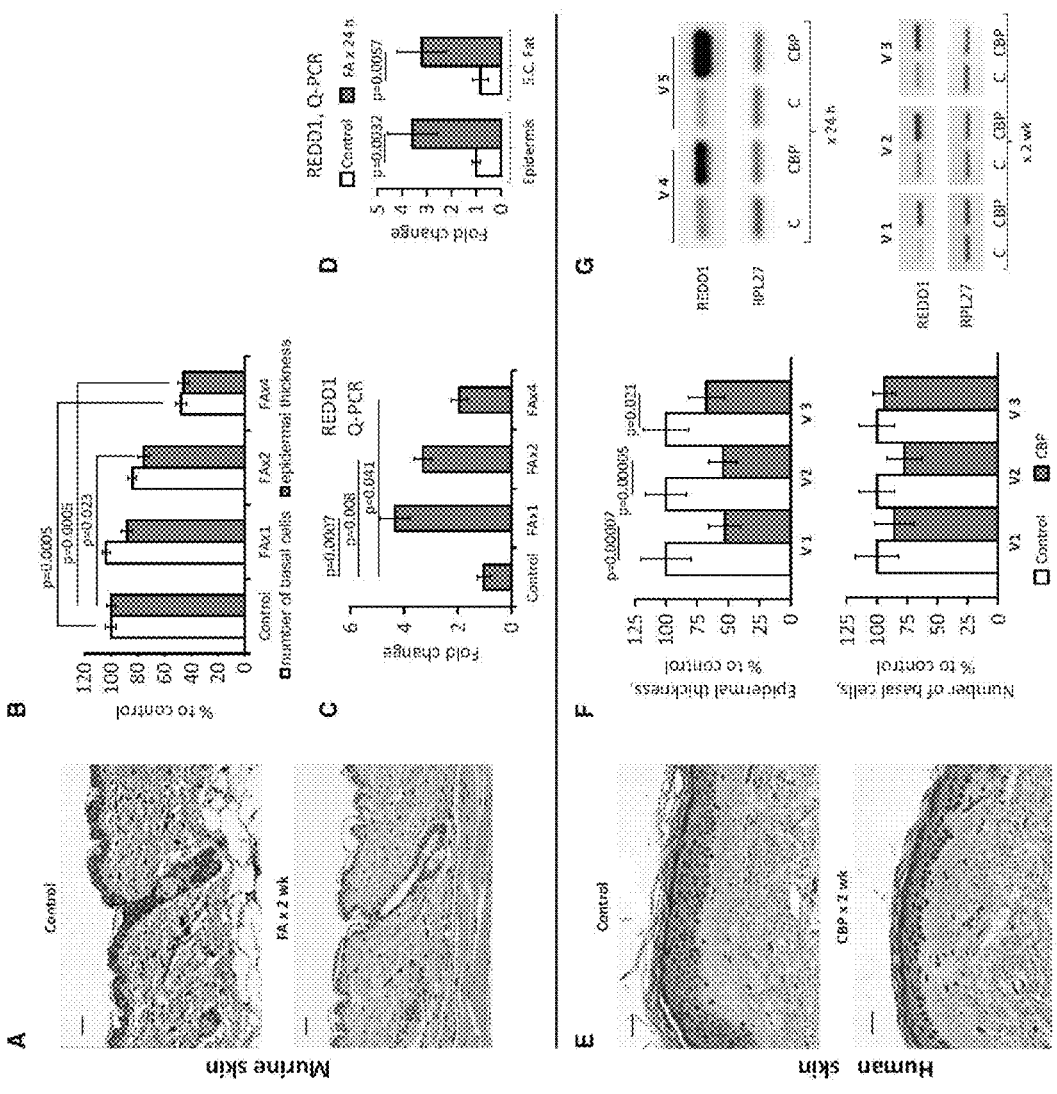
FIG. 1. Topical glucocorticoids induce epidermal atrophy and REDD1 mRNA expression. A-G B6D2 mice were treated topically with acetone (vehicle control) or glucocorticoid FA (2 µg/animal), every 72 h for 2 weeks. Human volunteers were treated with 0.05% CPB cream applied to the right arm skin once or daily for 2 weeks. Untreated skin from the left arm was used as a control. H&E staining of mouse skin (A) and human skin (E). Scale bars are 20 µm (A) and 40 µm (E). Morphometric analysis of epidermal thickness and number of basal keratinocytes in mouse skin treated with FA 1, 2, and 4 times (B), and human skin treated daily for 2 weeks (F). REDD1 mRNA expression in mouse epidermis 8 h after $1^{st}$, $2^{nd}$, and $4^{th}$ applications of FA (C, Q-PCR), in mouse epidermis and s.c. adipose, 24 h after FA (D, Q-PCR), and in human skin 24 h after single (G, volunteers V4 and V5) and 2-week (G, volunteers V1, V2, V3, RT-PCR) treatment with CBP. RPL27 was used as a cDNA normalization control. In human skin, the means±SD were calculated in each individual sample compared to the untreated skin from the same individual (30 measurements/condition). In mouse skin, the means±SD were calculated for three individual skin samples/condition in one representative experiment (30 measurements/condition) out of three experiments. Q-PCR results are the means±SD calculated for three individual RNA samples/condition. Statistical analysis for differences between treatment and control was done by the unpaired two-tailed t-test.

The present invention is described herein using several definitions, as set forth below and throughout the application.

Unless otherwise specified or indicated by context, the terms "a", "an", and "the" mean "one or more." For example, "a REDD1 inhibitor" should be interpreted to mean "one or more REDD1 inhibitors." Similarly, "a GR agonist" should be interpreted to mean "one or more GR agonists."

As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

As used herein, the phrase "effective amount" shall mean that drug dosage that provides the specific pharmacological response for which the drug is administered in a significant number of patients in need of such treatment. An effective amount of a drug that is administered to a particular patient in a particular instance will not always be effective in treating the conditions/diseases described herein, even though such dosage is deemed to be a therapeutically effective amount by those of skill in the art.

As used herein, a "patient" may be interchangeable with "subject" or "individual" and means an animal, which may be a human or non-human animal, in need of treatment. Non-human animals may include dogs, cats, horses, cows, pigs, sheep, and the like.

A "patient in need thereof" may include a patient having a disease, disorder, or condition that is responsive to modulation of GR expression or GR activity. Modulation may include induction of GR activity or inhibition of GR activity. For example, a "patient in need thereof" may include a patient having a disease, disorder, or condition that is responsive to a treatment method that includes induction of GR protein expression or induction of GR transrepression activity.

A "patient in need thereof" may include a patient having or at risk for developing an inflammatory disease or disorder. A patient having or at risk for developing an inflammatory disease or disorder may include a patient having or at risk for developing asthma, arthritis, psoriasis, and dermatitis.

A "patient in need thereof" may include a patient having or at risk for developing a cancer. A patient having or at risk for developing a cancer may include a patient having or at risk for developing a blood cancer, for example, leukemia or myeloma.

The disclosed methods typically include administering an effective amount of an inhibitor of regulated in development and DNA damage response protein 1 ("REDD1"). "REDD1" may be referred to in the art alternatively as "REDD-1," "RTP801," DNA-damage-inducible transcript 4 ("DDIT4"), or "Dig2," and human REDD1 or DDIT4 is referenced under Entrez number 54541 (mRNA RefSeq NM_019058; protein RefSeq NP_061931).

As disclosed herein, a REDD1 inhibitor includes any agent that inhibits expression and/or activity of REDD1. As used herein, a compound that inhibits expression and/or activity of REDD1 is a compound that reduces the level of REDD1 mRNA or protein in a cell or tissue, or reduces or eliminates one or more biological activities of REDD1. For example, an antisense compound targeting REDD1 inhibits expression of REDD1 by promoting the degradation of REDD1 mRNA, thereby reducing the level of REDD1 protein.

In some embodiments, a REDD1 inhibitor can be a small molecule, nucleic acid, nucleic acid analogue, protein, antibody, peptide, aptamer or variants or fragments thereof. Suitable REDD1 inhibitors may include but are not limited to levamisole, clofazimine, metronidazole, bucladesine, tenoxicam, physostigmine, rapamycin, and pharmaceutically acceptable salts thereof. Suitable REDD1 inhibitors (i.e., "RTP801 inhibitors") may include inhibitors disclosed in U.S. Pat. Nos. 8,765,931; 8,642,571; 8,309,532; 8,067,570; and 7,741,299; and U.S. Published Application Nos. 2013/0095117; 2012/0156208; and 2011/0117102; the contents of which are incorporated by reference in their entireties.

In some embodiments of the disclosed methods, a REDD1 inhibitor that inhibits expression of REDD1 mRNA is administered. Suitable inhibitors may include inhibitory nucleic acid molecules (e.g., siRNA, shRNA, or miRNA). For example, in the disclosed methods expression of REDD1 mRNA may be inhibited by at least 10%, at least 25%, at least 50%, at least 75%, at least 90%, or at least 95% relative to a control. The REDD1 inhibitor may knockdown expression of REDD1. For example, a REDD1 inhibitor may knockdown expression of REDD1 by at least about 20%, 50%, 75% or higher (e.g., by about 80%, 81%, 82%, 83%, 84%, 85%, 86%, 87%, 88%, 89%, 90%, 91%, 92%, 93%, 94%, 95%, 96%, 97%, 98%, or 99%).

As another example, an antibody or small molecule that specifically binds or targets REDD1 may inhibit activity of REDD1 by directly inhibiting its biological activity or by preventing REDD1 protein from interacting with another protein, such as a transcription factor. In some embodiments or the methods, a REDD1 inhibitor is administered and REDD1 activity is inhibited by at least 10%, at least 25%, at least 50%, at least 75%, at least 90%, or at least 95% relative to an untreated control.

The compounds and compositions disclosed herein may modulate GR expression (e.g., expression of the GR protein), and/or the compounds and compositions disclosed herein may modulate GR activity. Glucocorticoid receptor activity may include one or more of ligand binding (e.g., GR binding to a GR agonist), GR-transactivation of target genes, and/or GR-transrepression of target genes.

The disclosed methods typically include administering a GR agonist. Suitable GR agonists may include naturally occurring or synthetic ligands for the GR receptor, such as but not limited to cortisone, cortisol (hydrocortisone), corticosterone, deoxycorticosterone acetate (DOCA), fluticasone propionate, fluocinolone acetonide (FA), GSK9027, prednisone, prednisolone, methylpredinosolone, dexamethasone, betamethasone, triamcinolone, beclometasone, fludrocortisone acetate, mometasone furoate, clobetasol propionate, isoflupredone, fludrocortisone, diflorasone, prednicarbate, aclometasone, halcinonide, fludroxycortide, fluorometholone, budesonide, flumetasone, desoxycortone, medrysone, rimexonlone, flunisolide, and pharmaceutically acceptable salts thereof.

The compounds utilized in the methods disclosed herein may be formulated as pharmaceutical compositions that include: (a) a therapeutically effective amount of one or more compounds as disclosed herein; and (b) one or more pharmaceutically acceptable carriers, excipients, or diluents. The pharmaceutical composition may include the compound in a range of about 0.1 to 2000 mg (preferably about 0.5 to 500 mg, and more preferably about 1 to 100 mg). The pharmaceutical composition may be administered to provide the compound at a daily dose of about 0.1 to 100 mg/kg body weight (preferably about 0.5 to 20 mg/kg body weight, more preferably about 0.1 to 10 mg/kg body weight). In some embodiments, after the pharmaceutical composition is administered to a patient (e.g., after about 1, 2, 3, 4, 5, or 6 hours post-administration), the concentration of the compound at the site of action is about 2 to 10 μM. The pharmaceutical compositions may be administered under any suitable regimen (e.g., once a day, twice a day, and three times a day).

The compounds utilized in the methods disclosed herein may be formulated as a pharmaceutical composition in solid dosage form, although any pharmaceutically acceptable dosage form can be utilized. Exemplary solid dosage forms include, but are not limited to, tablets, capsules, sachets, lozenges, powders, pills, or granules, and the solid dosage form can be, for example, a fast melt dosage form, controlled release dosage form, lyophilized dosage form, delayed release dosage form, extended release dosage form, pulsatile release dosage form, mixed immediate release and controlled release dosage form, or a combination thereof.

The compounds utilized in the methods disclosed herein may be formulated as a pharmaceutical composition that includes a carrier. For example, the carrier may be selected from the group consisting of proteins, carbohydrates, sugar, talc, magnesium stearate, cellulose, calcium carbonate, and starch-gelatin paste.

The compounds utilized in the methods disclosed herein may be formulated as a pharmaceutical composition that includes one or more binding agents, filling agents, lubricating agents, suspending agents, sweeteners, flavoring agents, preservatives, buffers, wetting agents, disintegrants, and effervescent agents. Filling agents may include lactose monohydrate, lactose anhydrous, and various starches; examples of binding agents are various celluloses and cross-linked polyvinylpyrrolidone, microcrystalline cellulose, such as Avicel® PH101 and Avicel® PH102, microcrystalline cellulose, and silicified microcrystalline cellulose (ProSolv SMCC™). Suitable lubricants, including agents that act on the flowability of the powder to be compressed, may include colloidal silicon dioxide, such as Aerosil®200, talc, stearic acid, magnesium stearate, calcium stearate, and silica gel. Examples of sweeteners may include any natural or artificial sweetener, such as sucrose, xylitol, sodium saccharin, cyclamate, aspartame, and acsulfame. Examples of flavoring agents are Magnasweet® (trademark of MAFCO), bubble gum flavor, and fruit flavors, and the like. Examples of preservatives may include potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride.

Suitable diluents may include pharmaceutically acceptable inert fillers, such as microcrystalline cellulose, lactose, dibasic calcium phosphate, saccharides, and mixtures of any of the foregoing. Examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

Examples of effervescent agents are effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

The compounds utilized in the methods disclosed herein may be administered in conventional dosage forms prepared by combining the active ingredient with standard pharmaceutical carriers or diluents according to conventional procedures well known in the art. These procedures may involve mixing, granulating and compressing or dissolving the ingredients as appropriate to the desired preparation.

The compounds utilized in the methods disclosed herein may be formulated as a pharmaceutical composition for delivery via any suitable route. For example, the pharmaceutical composition may be administered via oral, intravenous, intramuscular, subcutaneous, topical, and pulmonary route. Examples of pharmaceutical compositions for oral administration include capsules, syrups, concentrates, powders and granules.

Pharmaceutical compositions comprising the compounds may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions. Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavoring or coloring agents.

Pharmaceutical compositions adapted for transdermal administration may be presented as discrete patches intended to remain in intimate contact with the epidermis of the recipient for a prolonged period of time. For example, the active ingredient may be delivered from the patch by iontophoresis.

Pharmaceutical compositions adapted for topical administration may be formulated as ointments, creams, suspensions, lotions, powders, solutions, pastes, gels, impregnated dressings, sprays, aerosols or oils and may contain appropriate conventional additives such as preservatives, solvents to assist drug penetration and emollients in ointments and creams.

For applications to the eye or other external tissues, for example the mouth and skin, the pharmaceutical compositions are preferably applied as a topical ointment or cream. When formulated in an ointment, the compound may be employed with either a paraffinic or a water-miscible ointment base. Alternatively, the compound may be formulated in a cream with an oil-in-water cream base or a water-in-oil base. Pharmaceutical compositions adapted for topical administration to the eye include eye drops where the active ingredient is dissolved or suspended in a suitable carrier, especially an aqueous solvent.

Pharmaceutical compositions adapted for topical administration in the mouth include lozenges, pastilles and mouth washes.

Pharmaceutical compositions adapted for nasal administration where the carrier is a solid include a coarse powder having a particle size (e.g., in the range 20 to 500 microns) which is administered in the manner in which snuff is taken (i.e., by rapid inhalation through the nasal passage from a container of the powder held close up to the nose). Suitable formulations where the carrier is a liquid, for administration as a nasal spray or as nasal drops, include aqueous or oil solutions of the active ingredient.

Pharmaceutical compositions adapted for administration by inhalation include fine particle dusts or mists which may be generated by means of various types of metered dose pressurized aerosols, nebulizers or insufflators.

Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Illustrative Embodiments

The following embodiments are illustrative and should not be interpreted to limit the scope of the claimed subject matter.

Embodiment 1

A method comprising administering to a patient in need thereof a glucocorticoid receptor (GR) agonist and an inhibitor of regulated in development and DNA damage response protein 1 (REDD1 inhibitor), wherein the REDD1 inhibitor is administered before, concurrently with, or after the GR agonist is administered.

Embodiment 2

The method of embodiment 1, wherein the patient is administered an effective amount of the REDD1 inhibitor for reducing atrophy of epidermis, subcutaneous fat, or muscle.

Embodiment 3

The method of embodiment 1 or 2, wherein the patient has previously been administered a GR agonist and is exhibiting negative side effects of GR agonist therapy.

Embodiment 4

The method of embodiment 1 or 2, wherein the patient has not previously been administered a GR agonist.

Embodiment 5

The method of any of the foregoing embodiments, wherein the patient has an inflammatory disease or disorder.

Embodiment 6

The method of embodiment 5, wherein the inflammatory disease is selected from a group consisting of asthma, arthritis, psoriasis, and dermatitis.

Embodiment 7

The method of any of embodiments 1-4, wherein the patient has a cancer.

Embodiment 8

The method of embodiment 7, wherein the cancer is a blood cancer selected from a group consisting of leukemia and myeloma.

Embodiment 9

The method of any of the foregoing embodiments, wherein the GR agonist is selected from the group consisting of cortisone, cortisol, corticosterone, deoxycorticosterone acetate (DOCA), fluticasone propionate, fluocinolone acetonide (FA), GSK9027, prednisone, prednisolone, methylpredinosolone, dexamethasone, betamethasone, triamcinolone, beclometasone, fludrocortisone acetate, mometasone furoate, clobetasol propionate, and pharmaceutically acceptable salts thereof.

Embodiment 10

The method of any of the foregoing embodiments, wherein the REDD1 inhibitor is selected from the group consisting of levamisole, clofazimine, metronidazole, bucladesine, tenoxicam, physostigmine, rapamycin, and pharmaceutically acceptable salts thereof.

Embodiment 11

The method of any of the foregoing embodiments, wherein the REDD1 inhibitor inhibits expression of REDD1.

Embodiment 12

The method of embodiment 11, wherein the inhibitor is an inhibitory nucleic acid molecule.

Embodiment 13

The method of embodiment 12, wherein the inhibitory nucleic acid molecule is an siRNA or an shRNA.

Embodiment 14

The method of any of embodiments 1-10, wherein the REDD1 inhibitor inhibits activity of REDD1.

Embodiment 15

A pharmaceutical composition comprising: (i) a REDD1 inhibitor; (ii) a GR agonist; and (iii) an excipient, carrier, or diluent.

Embodiment 16

The composition of embodiment 15, wherein the GR agonist is selected from the group consisting of cortisone, cortisol, corticosterone, deoxycorticosterone acetate (DOCA), fluticasone propionate, fluocinolone acetonide (FA), GSK9027, prednisone, prednisolone, methylpredinosolone, dexamethasone, betamethasone, triamcinolone, beclometasone, fludrocortisone acetate, mometasone furoate, clobetasol propionate, and pharmaceutically acceptable salts thereof.

Embodiment 17

The composition of embodiment 15, wherein the REDD1 inhibitor is selected from the group consisting of levamisole, clofazimine, metronidazole, bucladesine, tenoxicam, physostigmine, rapamycin, and pharmaceutically acceptable salts thereof.

Embodiment 18

A kit for treating or preventing negative side effects of therapy with a GR agonist, the kit comprising: (i) a dose of a REDD1 inhibitor; and (ii) a dose of the GR agonist.

Embodiment 19

The kit of embodiment 18, wherein the GR agonist is selected from the group consisting of cortisone, cortisol, corticosterone, deoxycorticosterone acetate (DOCA), fluticasone propionate, fluocinolone acetonide (FA), GSK9027, prednisone, prednisolone, methylpredinosolone, dexamethasone, betamethasone, triamcinolone, beclometasone, fludrocortisone acetate, mometasone furoate, clobetasol propionate, and pharmaceutically acceptable salts thereof.

Embodiment 20

The kit of embodiment 18, wherein the REDD1 inhibitor is selected from the group consisting of levamisole, clofazimine, metronidazole, bucladesine, tenoxicam, physostigmine, rapamycin, and pharmaceutically acceptable salts thereof.

EXAMPLES

The following Examples are illustrative and are not intended to limit the scope of the claimed subject matter.

Example 1

Reference is made to Baida et al., "Glucocorticoids induce epidermal atrophy via activation of REDD1 and inhibition of m-TOR activity," 2012 SID Annual Meeting Abstracts, May 9-12, 2012, J. Invest. Derma. (2012) 132, S51-S64, doi:10.1038/jid.2012.83, which is incorporated by reference in its entirety.

Example 2

Reference is made to Lesovaya et al., "Activation of nutritional sensor REDD1 is necessary for the development of steroid-induced cutaneous atrophy," 42$^{nd}$ Annual ESDR Meeting Abstracts, Sep. 19-22, 2012, J. Invest. Derma. (2012) 132, S100-S103, doi:10.1038/jid.2012.303, which is incorporated by reference in its entirety.

Example 3

Reference is made to Baida et al., "Activation of nutritional sensor REDD1 is necessary for the development of steroid-induced cutaneous atrophy," 5$^{th}$ Great Lakes Nuclear Receptor Conference (GLNRC), Oct. 12-13, 2012, which is incorporated by reference in its entirety.

Example 4

Reference is made to Baida et al., "Deletion of mTOR inhibitor REDD1 protects CD34+ follicular epithelial stem cells and prevents development of steroid-induced cutaneous atrophy," 2013 International Investigative Dermatology Meeting, May 8-11, 2013, J. Invest. Derma. (2013) 133, S243-246, doi:10.1038/jid.2013.106, which is incorporated by reference in its entirety.

Example 5

Reference is made to Baida et al., "REDD1 functions at the crossroads between the therapeutic and adverse effects of topical glucocorticoids," EMBO Molec. Med. (2015) 7:42-58, (hereinafter "Baida et al. EMBO, 2015"), published online Dec. 11, 2014, which is incorporated by reference in its entirety.

Abstract

Cutaneous atrophy is the major adverse effect of topical glucocorticoids; however, its molecular mechanisms are poorly understood. Here, we identify stress-inducible mTOR inhibitor REDD1 (regulated in development and DNA damage response 1) as a major molecular target of glucocorticoids, which mediates cutaneous atrophy. In REDD1 knockout (KO) mice, all skin compartments (epidermis, dermis, subcutaneous fat), epidermal stem, and progenitor cells were protected from atrophic effects of glucocorticoids. Moreover, REDD1 knockdown resulted in similar consequences in organotypic raft cultures of primary human keratinocytes. Expression profiling revealed that gene activation by glucocorticoids was strongly altered in REDD1 KO epidermis. In contrast, the down-regulation of genes involved in anti-inflammatory glucocorticoid response was strikingly similar in wild-type and REDD1 KO mice. Integrative bioinformatics analysis of our and published gene array data revealed similar changes of gene expression in epidermis and in muscle undergoing glucocorticoid-dependent and glucocorticoid-independent atrophy Importantly, the lack of REDD1 did not diminish the anti-inflammatory effects of glucocorticoids in preclinical model. Our findings suggest that combining steroids with REDD1 inhibitors may yield a novel, safer glucocorticoid-based therapies.

Introduction

Glucocorticoid hormones are essential regulators of proliferation, differentiation, and metabolism in skin. They are also effective anti-inflammatory drugs widely used to treat the hyperproliferative and inflammatory skin diseases such as atopic dermatitis and psoriasis (Schäcke et al, 2006; Schoepe et al, 2006). Unfortunately, their beneficial therapeutic effects are often accompanied by numerous adverse effects including skin atrophy, characterized by a profound loss in skin thickness and elasticity combined with decreased barrier function. Skin atrophy involves all skin compartments, that is, epidermis, dermis, sebaceous glands, and subcutaneous (s.c.) fat. Typical epidermal changes include a reduction in thickness, decreased number and size of keratinocytes, diminished stratum corneum and intercellular lipid lamella (Jablonska et al, 1979; Lehmann et al, 1983; Zheng et al, 1984; Lubach & Kietzmann, 1988; Schoepe et al, 2006). These changes are combined with an altered orientation and packing of collagen and elastin fibers, and decreased cellularity in the dermis (Lehmann et al, 1983; Schoepe et al, 2006). In addition, in mice topical glucocorticoids and in patients intradermally injected glucocorticoids induce drastic atrophy/lypolysis of s.c. fat (Woodbury & Kligman, 1992; Imagawa & Ohkuma, 2010). Although steroid-induced skin atrophy is well known and characterized morphologically, the underlying molecular mechanisms are poorly understood.

Glucocorticoids act via a specific receptor (the glucocorticoid receptor, GR), which is a ligand-dependent transcription factor (Adcock, 2001; Necela & Cidlowski, 2004; Vandevyver et al, 2012; Ratman et al, 2013). In the absence of glucocorticoids, GR resides in the cytoplasm in a complex with molecular chaperones that inhibit GR nuclear import. Upon ligand binding, GR undergoes phosphorylation, dimerization, and nuclear translocation. Gene transactivation (TA) by glucocorticoids requires binding of GR homodimers to palindromic glucocorticoid-responsive elements (GRE) in gene promoters. Transrepression (TR) by glucocorticoids is mediated by diverse mechanisms including interaction between GR and other transcription factors, such as major pro-inflammatory factors NF-κB and AP-1 (De Bosscher et al, 2003; Necela & Cidlowski, 2004; Schäcke et al, 2006; Chebotaev et al, 2007a; Ratman et al, 2013). TR by GR is critical for anti-inflammatory effects of glucocorticoids. In contrast, many metabolic side effects of oral steroids related to the maintenance of the hypothalamic-pituitary-adrenal axis, glucose metabolism, and osteoporosis are largely dependent on TA (Schäcke et al, 2006, 2009; De Bosscher et al, 2010; Nixon et al, 2013; Ratman et al, 2013).

We discovered recently that glucocorticoids induced a robust activation of REDD1 (regulated in development and DNA damage response) in mouse and human skin (Baida et al, 2013). REDD1 is a stress response gene induced by hypoxia, DNA damage, nutrient or energy deprivation, or by endoplasmic reticulum stress (Shoshani et al, 2002; Ellisen et al, 2002; Brugarolas et al, 2004; Lin et al, 2005; Sofer et al, 2005; Wang et al, 2006; DeYoung et al, 2008). REDD1 is also activated by glucocorticoids and is a direct GR target (Wang et al, 2006; Shimizu et al, 2011). It inhibits mammalian target of rapamycin (mTOR) by stabilizing the tuberous sclerosis protein 1 (TSC1)-TSC2 inhibitory complex (Brugarolas et al, 2004; Ellisen, 2005; Wang et al, 2006; DeYoung et al, 2008; Mata et al, 2011). mTOR regulation by REDD1 contributes to the control of cell growth and size in Drosophila and in mammals. These findings suggest that abnormalities of REDD1 signaling may disrupt energy homeostasis (Ellisen et al, 2002; Shoshani et al, 2002; Sofer et al, 2005; Katiyar et al, 2009).

REDD1 is involved in another atrophogenic effect of glucocorticoids, muscle waste (Wang et al, 2006; Shimizu et al, 2011). It is also well understood that cross-talk between anabolic mTOR and catabolic GR is important to maintain the mass of skeletal muscle (Shimizu et al, 2011). Such cross-talk, as well as the role of REDD1 in steroid-induced atrophy in the skin, has not been considered.

REDD1 KO mice (Brafman et al, 2004; Sofer et al, 2005) are resistant to a variety of pathological conditions caused by stress, such as oxidative stress in the retina, emphysema induced by tobacco smoke, and ceramide-induced apoptosis of the lung epithelial cells (Brafman et al, 2004; Yoshida et al, 2010; Kamocki et al, 2013). However, neither adverse nor therapeutic effects of glucocorticoids have been studied on REDD1 KO background.

Here, we used REDD1 KO mice to examine the role of REDD1 in skin. We report that REDD1 KO animals are resistant to glucocorticoid-induced skin atrophy compared to wild-type isogenic animals. Similarly, organotypic raft cultures of primary human keratinocytes after REDD1 knockdown were completely protected from the hypoplastic effects of glucocorticoids. In contrast, REDD1 was dispensable for the anti-inflammatory action of glucocorticoids. In agreement, the comparison of transcriptional response to glucocorticoids in the epidermis of wild-type and REDD1 KO mice revealed that REDD1 is critically important for the TA by the glucocorticoids, especially the genes related to lipid and protein metabolism/catabolism, but not for the TR of the genes related to glucocorticoid anti-inflammatory effects.

Results

Topical Glucocorticoids Induce Skin Atrophy and Activate REDD1 Expression.

We used clinically relevant glucocorticoid regiments known to induce significant skin atrophy in mice and in patients (Schoepe et al, 2006, 2010; Chebotaev et al, 2007b). B6D2 mice (F1 C57Bl/6×DBA) that we used previously to study the side effects of glucocorticoids (Chebotaev et al, 2007b) were treated with medium potency glucocorticoid fluocinolone acetonide (FA, 2 µg/animal). For human volunteers, we used one of the most potent steroids, clobetasol propionate (CBP, 0.05% cream). In mice, a 2-week treatment caused a marked 50% epidermal thinning and 50% depletion of the interfollicular basal keratinocytes (FIGS. 1A, B). A similar degree of epidermal hypoplasia was observed in humans after 2-week treatment; however, the negative effect on basal keratinocytes was less pronounced (FIGS. 1E, F).

We recently reported that REDD1 was at the top of the list of genes up-regulated in mouse epidermis upon FA treatment (Baida et al, 2013). Using Q-PCR, we showed that REDD1 mRNA was increased by ~4.5-fold in the epidermis of B6D2 mice, 4-24 h after the first FA application (FIGS. 1C, D), and stayed significantly above the control level for the duration of treatment. REDD1 mRNA was also strongly up-regulated in human skin treated with CBP for 24 h-2 weeks (FIG. 1G).

Because the atrophic changes in mouse epidermis due to FA treatment were paralleled by the complete depletion of s.c. adipose tissue (FIG. 1A), we assessed REDD1 in adipose. The purity of s.c. adipose isolation was verified using specific adipocyte and keratinocyte markers (Supplementary FIG. S1). We found that REDD1 expression was equally activated in s.c. adipose and epidermis (FIG. 1D and Baida et al., EMBO, 2015, at Supplementary FIG. S1).

REDD1 Protein Level is Tightly Regulated in Epidermis and Correlates with mTOR Activity and Autophagy.

Figure 2:
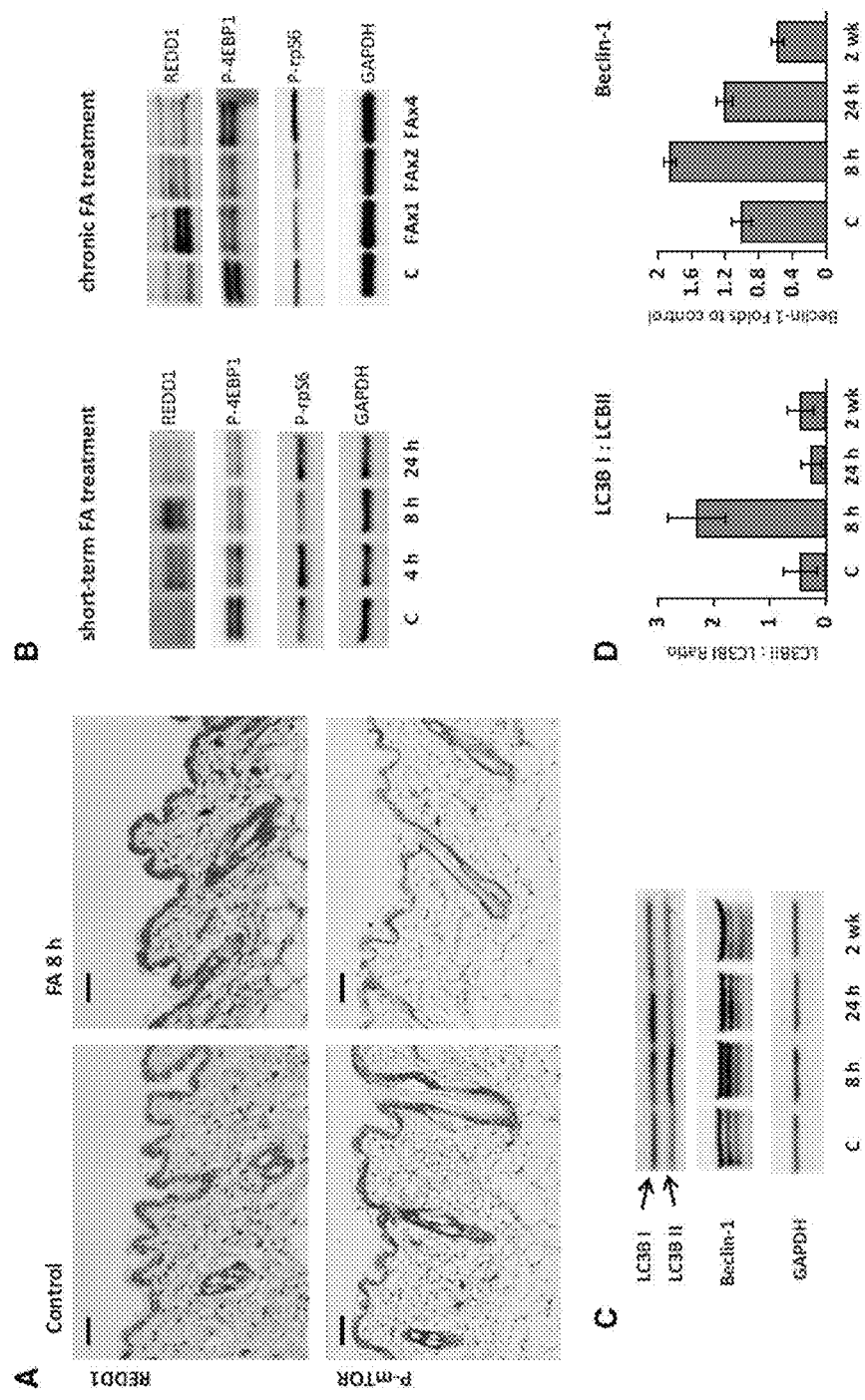
FIG. 2. REDD1 protein expression in epidermis is tightly regulated and correlates with inhibition of mTOR and autophagy. B6D2 mice were treated topically as in FIG. 1. Skin was harvested 4-24 h after single FA application or during chronic treatment (8 h after $1^{st}$, $2^{nd}$, and $4^{th}$ applications). A Immunohistochemical staining of mouse skin treated with acetone or FA for 8 h for REDD1 (upper panels) and phosphorylated mTOR-Ser2448 (lower panels). Scale bars are 20 µm. B. Western blot analysis of REDD1 protein and phosphorylation of down-stream mTOR target proteins 4E-BP1 and rpS6 in murine epidermis. GAPDH is used as a normalization control. C, D. Glucocorticoids induce autophagy in epidermis. Western blot analysis of Beclin-1 and conversion of light chain 3 (LC3) from LC3-I to LC3-II (C). Quantification of LC3-I to LC3-II conversion and Beclin-1 expression (D). The means±SD were calculated using Western blots from two independent experiments (each lane is whole-cell protein from three pulled individual samples of epidermis).

Both immunostaining and Western blot analysis revealed that REDD1 protein was barely detectable in the skin of adult wild-type mice (FIGS. 2A, B). FA induced REDD1 expression as early as 4-8 h after first application and following subsequent applications during chronic FA treatment, albeit to a lesser extent (FIG. 2B). The multiband pattern of REDD1 signal on Western blots was reported previously and may reflect REDD1 phosphorylation (Katiyar et al, 2009; Li et al, 2012; Regazzetti et al, 2012). The increase in REDD1 protein in the skin in response to FA was confirmed by immunostaining, which showed that REDD1 was mostly expressed in the cytoplasm of mouse keratinocytes throughout the epidermis (FIG. 2A).

Figure 9:
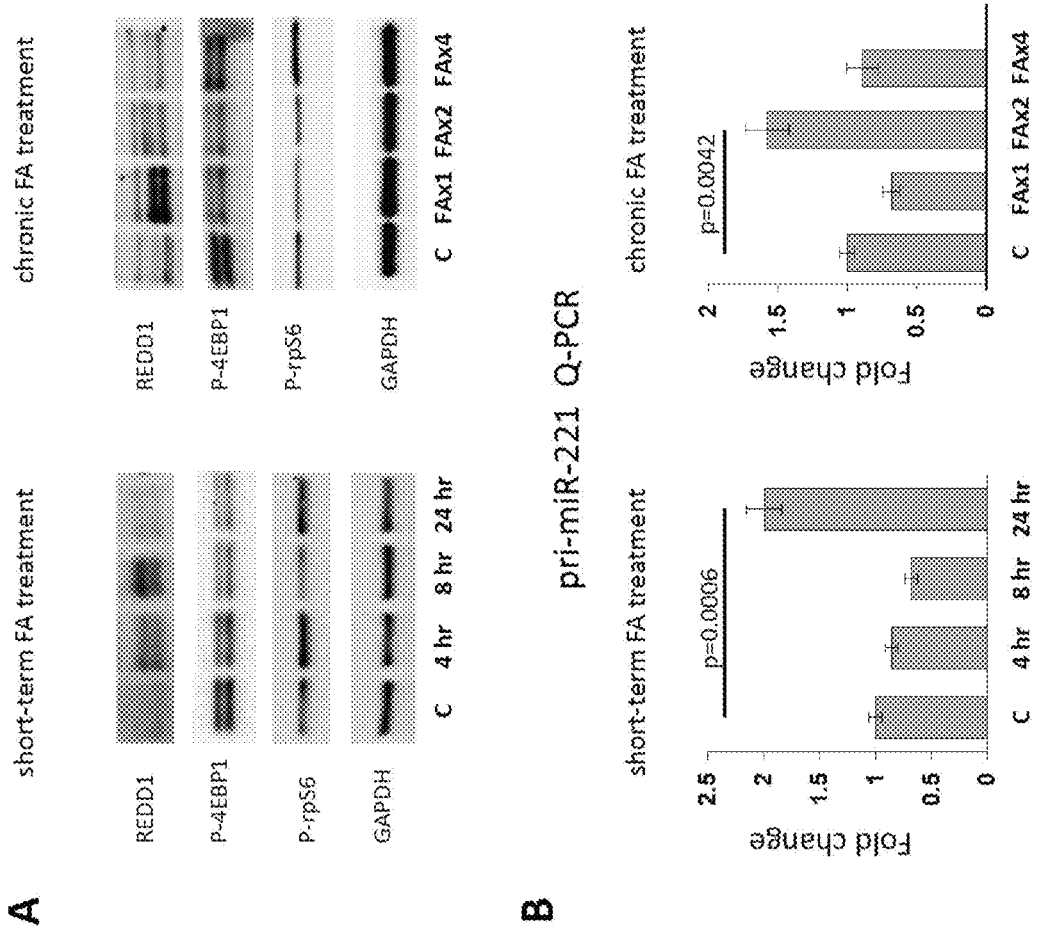
FIG. 9. Inverse correlation between pri-miR-221 and REDD1 expression during glucocorticoid treatment. B6D2 mice were treated with FA topically as described in Materials and Methods, epidermis was harvested at indicated time points. A. Western blot analysis. B. Q-PCR analysis of primary miR-221. Data are expressed as the fold change (mean±SD) with respect to the controls (unpaired two-tailed t-test, n=3).

The observed differences between REDD1 induction dynamics at mRNA and protein levels (especially at the 24-h time point and at the end of chronic FA treatment, compare FIGS. 1C, D, and FIG. 2B) are likely due its short half-life (Katiyar et al, 2009). REDD1 expression is regulated via multiple mechanisms including translational repression by miR-221 which was reported to regulate REDD1 in murine hepatic progenitor cells (Pineau et al, 2010). In agreement, pri-miR-221 was significantly increased at the time points when REDD1 protein levels started to decline, for example, 24 h after single FA application, and after the first week of the chronic treatment (FIG. 9). This inverse correlation suggests that mature miR-221 is possibly involved in control of REDD1 induction by steroids in skin.

Because REDD1 is a known inhibitor of mTOR signaling (Sofer et al, 2005; Wang et al, 2006; DeYoung et al, 2008; Shimizu et al, 2011), we tested whether FA inhibits mTOR activity in the skin. In previous studies, mTOR activity has been monitored by phosphorylation of its major substrates, 4E-BP1 (eukaryotic initiation factor 4E binding protein 1) and S6K1 (ribosomal p70/S6 kinase 1) as well as ribosomal protein S6 (rpS6), a substrate of S6K1 (Checkley et al, 2011). As basal level of S6K1 phosphorylation was low in skin of B6D2 mice, we used 4E-BP1 and rpS6 as preferred markers. We showed that FA blocked mTOR activity in the skin. Moreover, there was an inverse correlation between phosphorylation of mTOR targets and REDD1 expression in the epidermis. By the time when REDD1 expression reached its peak (8 h after 1st and 2nd FA applications), the repression of mTOR activity by FA was most pronounced (FIGS.

2A, B). We further confirmed this inverse correlation using immunostaining for REDD1 and active, phosphorylated at Ser2448 mTOR (FIG. 2A).

Previous studies showed that mTOR inhibition by glucocorticoids in other tissues causes autophagy (Molitoris et al, 2011; Shimizu et al, 2011). In accordance, we observed in FA-treated skin the conversion of light chain 3 (LC3) from its free form (LC3-I) to a membrane-bound state (LC3-II), a key step that initiates autophagy in mammalian cells (Klionsky et al, 2012). LC3-I to LC3-II conversion reached its maximum 8 h after FA treatment and paralleled with the increase of another autophagy marker Beclin-1, highest REDD1 expression and strongest repression of mTOR activity (FIGS. 2C, D).

REDD1 KO Mice are Resistant to the Depletion of Stem Cells and Skin Atrophy by Glucocorticoids.

Figure 3:
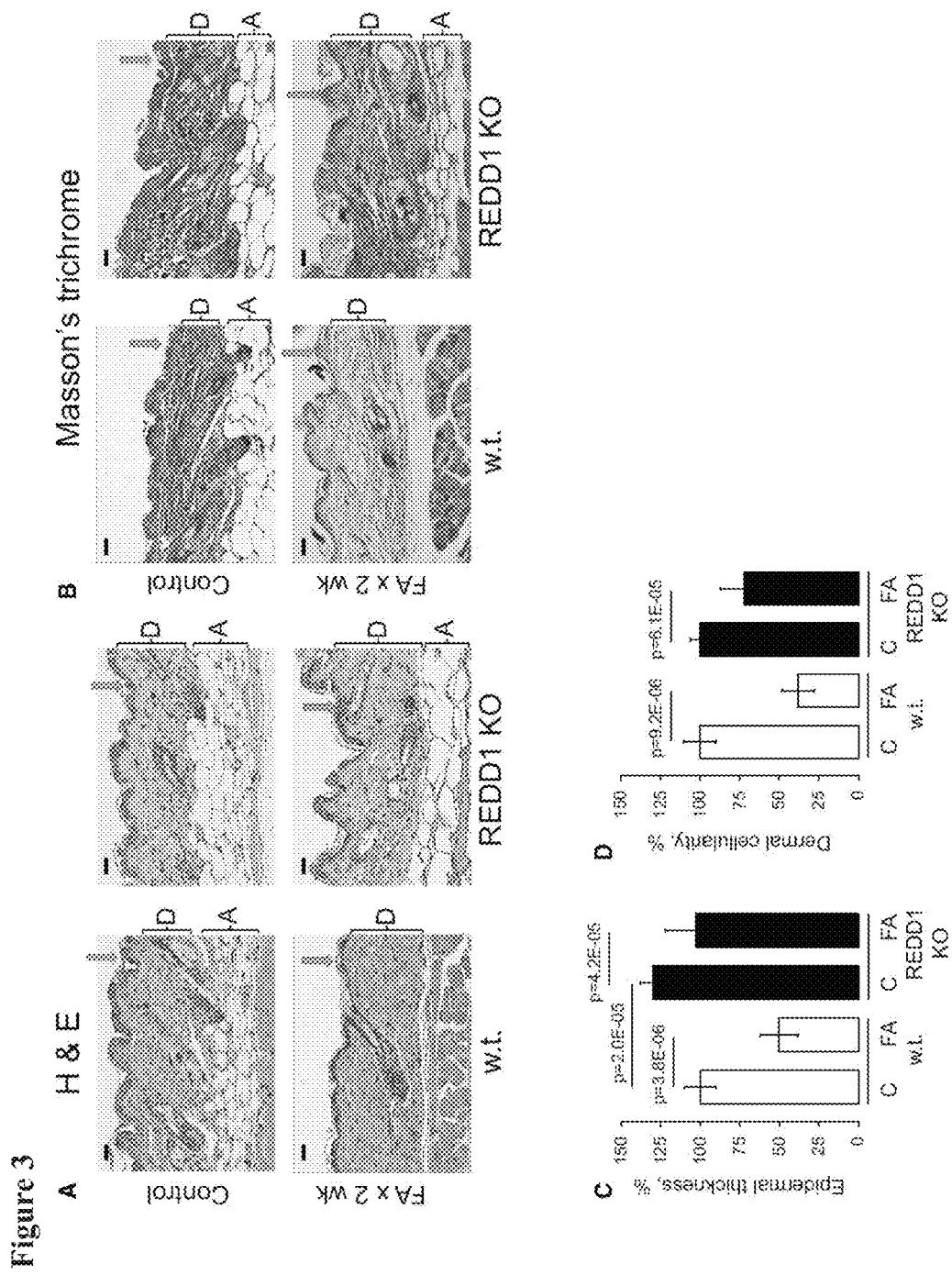
FIG. 3. REDD1 KO mice are resistant to glucocorticoid-induced skin atrophy. REDD1 KO and isogenic wild-type B6×129 mice were treated with acetone (vehicle control) or FA (2 µg/animal) every 72 h for 2 weeks. A, B. H&E staining (A) and Masson's trichrome staining: Dermis/collagen fibers are blue, muscle is red, nuclei are dark red, and cytoplasm is red/pink (B). Arrows point to epidermis and brackets indicate subcutaneous adipose (A) and dermis (D). Scale bars are 20 µm. C, D. Morphometric analysis of epidermal thickness and dermal cellularity as described in Materials and Methods. Changes in epidermal thickness (C) are presented as % to wild-type control epidermis. Changes in dermal cellularity (D) are presented as % to corresponding control skin. The means±SD were calculated for three individual skin samples in one representative experiment (30 measurements/condition) out of two experiments. Statistical analysis for differences between treatment and control and between control wild-type and REDD1 KO epidermal thickness was done by the unpaired two-tailed t-test.

To assess the causative role of REDD1 in therapeutic and side effects of glucocorticoids in the skin, we compared REDD1 KO mice (Brafman et al, 2004) with isogenic controls (B6×129). REDD1 KO mice displayed mild epidermal hyperplasia and slightly increased keratinocyte proliferation (FIG. 3C and data not shown). There were no significant changes in early and medium/late differentiation markers including keratins K5, K10, loricrin, and involucrin (data not shown, see Baida et. al., EMBO 2015 at Supplementary FIG. S2).

Figure 10:
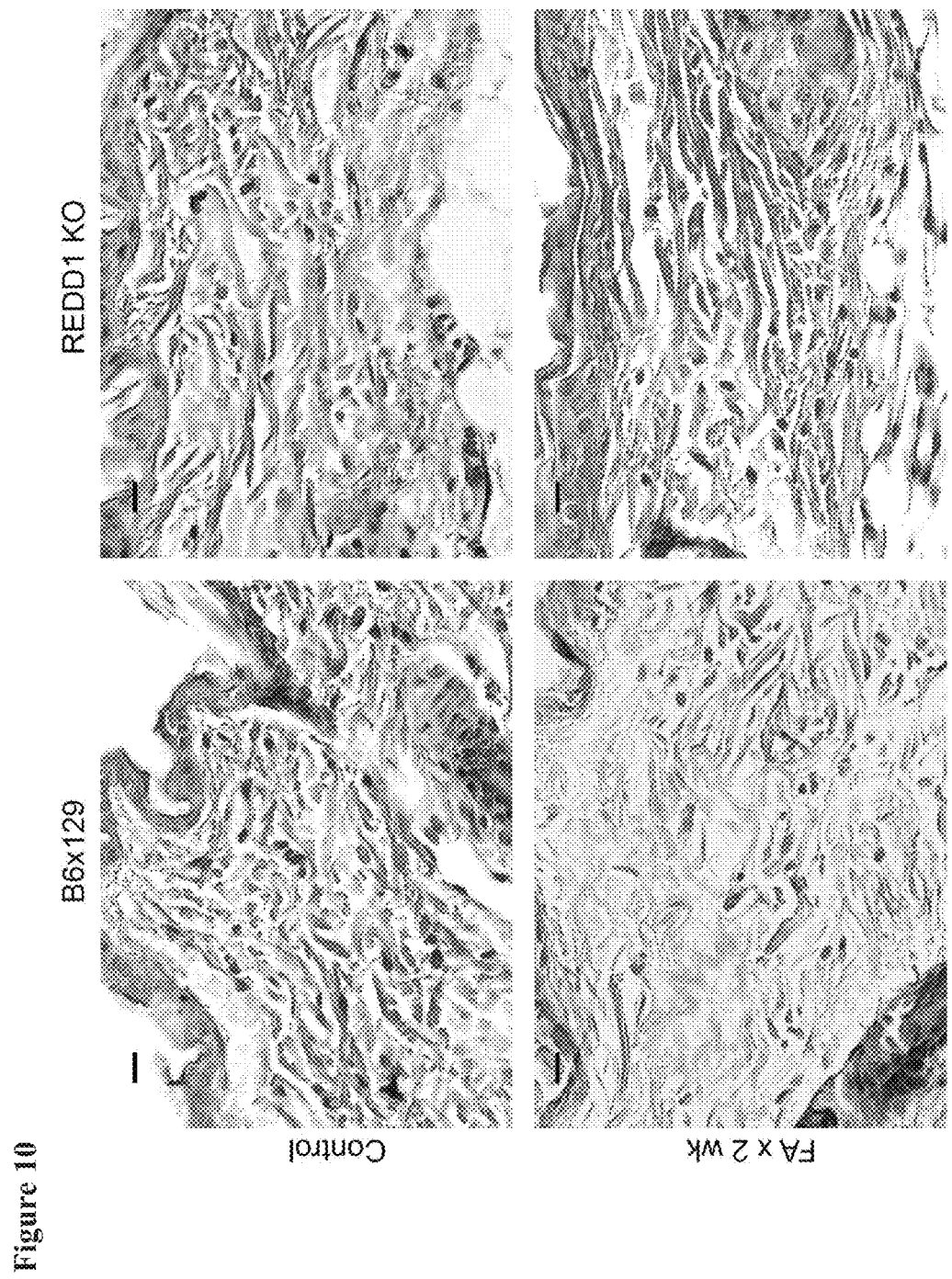
FIG. 10. Resistance of REDD1 KO mice to glucocorticoid-induced decrease of dermal cellularity. REDD1 KO and isogenic w.t. B6×129 mice were treated with acetone (vehicle control) or FA (2 µg/animal) every 72 hr for 2 wk. Formalin-fixed paraffin-embedded skin sections were used for Masson's trichrome staining Dermis/collagen fibers are blue, muscle is red, nuclei are dark red, and cytoplasm is red/pink. Scalebars are 40 µm. Note: strongly decreased number of dermal fibrobalsts in the skin of w.t. mice treated with FA×2 wk.

In contrast, the lack of REDD1 strongly attenuated the effects of glucocorticoids in the skin. REDD1 KO animals showed considerable resistance to FA-induced epidermal atrophy compared to wild-type animals. In wild-type mice, chronic FA treatment reduced epidermal thickness by 50%, compared to <20% in REDD1 KO mice (FIGS. 3A, C). Similarly, s.c, adipose tissue was significantly protected from the atrophy upon REDD1 knockout (FIGS. 3A, B). Glucocorticoids induce severe thinning of collagen and elastin fibrous network and decrease cellularity of the dermis (Woodbury & Kligman, 1992; Schoepe et al, 2006). Using Masson's trichrome staining, we showed that REDD1 KO minimized FA effect on dermal fibers and caused significant protection of the dermal cells (FIGS. 3B, D, and higher magnification images in FIG. 10.

Figure 4:
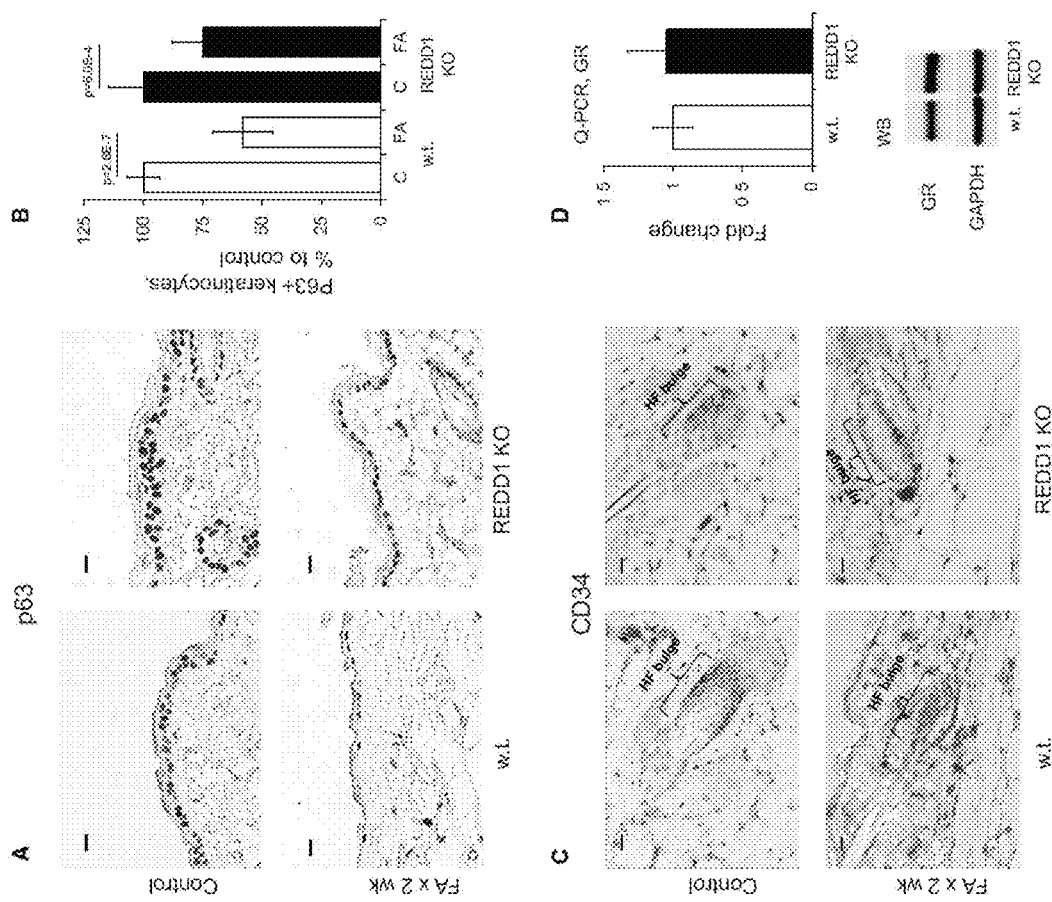
FIG. 4. Protective effect of REDD1 KO on p63[+] progenitors and CD34[+] follicular epithelial stem cells. REDD1 KO and wild-type animals were treated as in FIG. 3. A-C. Expression of p63 (A) and CD34 (C). Scale bars are 10 µm. Analysis of p63 staining (B). The number of p63[+] basal keratinocytes/total number of basal keratinocytes is presented as % to the corresponding control epidermis. D. Similar GR expression in epidermis of wild-type and REDD1 KO mice determined by Q-PCR and Western blotting. Rp127 and GAPDH used as a normalization controls, respectively. Data information: The means±SD were calculated for three individual skin samples in one representative experiment (30 measurements/condition) out of two experiments. Q-PCR results are presented as the means±SD for three individual RNA samples/condition. Statistical analysis for differences between treatment and control was done by the unpaired two-tailed t-test.

Our previous studies showed that GR activation has a profound negative effect on epidermal stem cells (SCs) in the bulge of hair follicles (Chebotaev et al, 2007b,c). In agreement, chronic FA treatment of wild-type mice completely eliminated the CD34+ follicular SCs (only 5% of hair follicles were CD34 positive) and diminished by ~40% the numbers of p63-positive progenitors in the basal layer of epidermis (FIGS. 4A, C) Importantly, in REDD1 KO animals treated with FA, CD34+ SCs and p63+ keratinocytes were largely preserved: 40% of hair follicles remained CD34 positive, and the number of p63+ basal keratinocytes decreased only by 20% (FIGS. 4A, C).

REDD1 KO Mice Retain Sensitivity to the Anti-Inflammatory Effect of Glucocorticoids.

Figure 5:
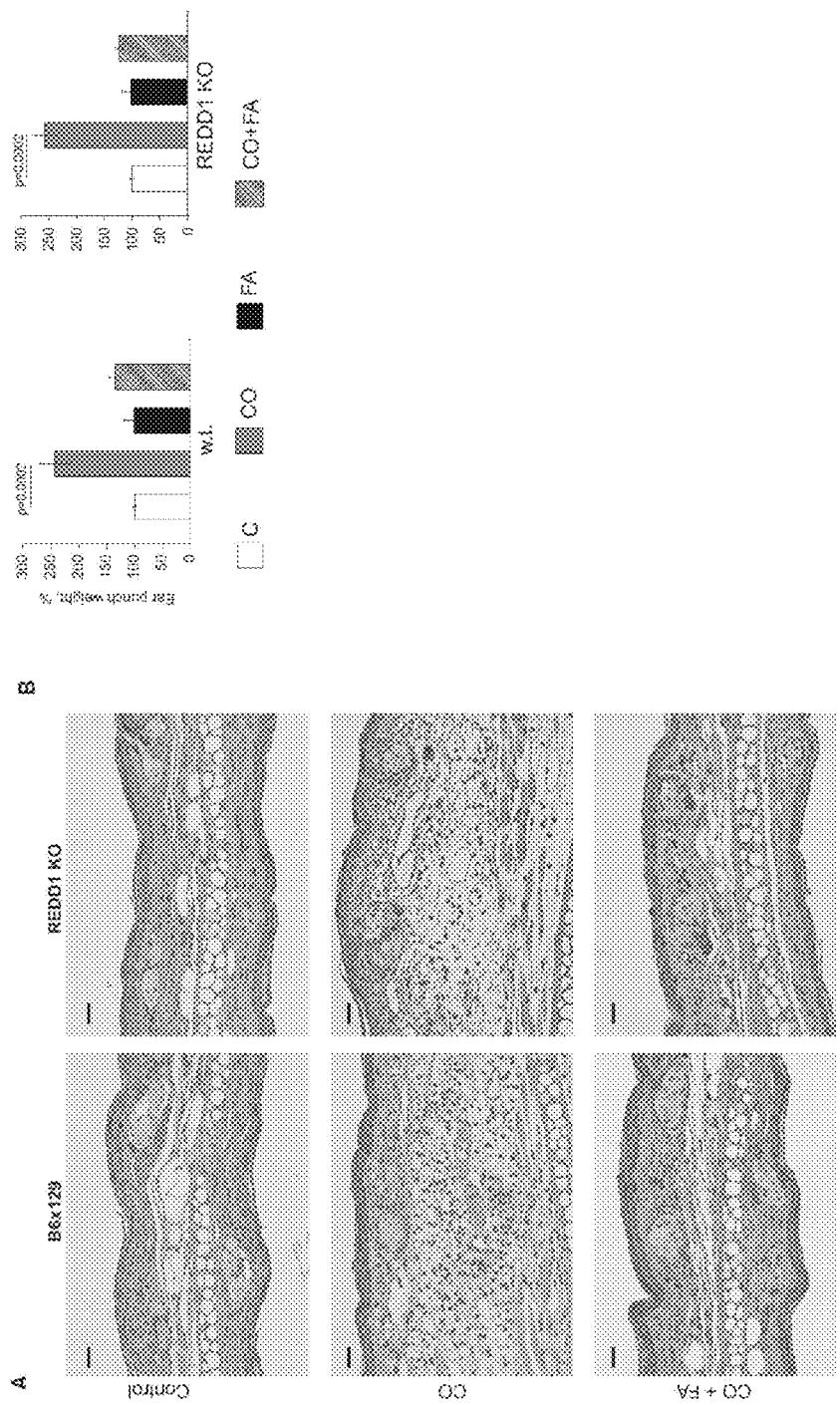
FIG. 5. Similar sensitivity of REDD1 KO and wild-type animals to the anti-inflammatory effect of glucocorticoids. Ear edema was induced by croton oil (CO) as in Materials and Methods. FA was applied 1 h before CO, and four-millimeter ear punch was weighed 9 h after CO application to assess swelling. In the additional experiment, ears were harvested 9 h after CO application and used for histological analysis. A. H&E staining Scale bars are 20 µm. B. Ear punch weight. Results are presented as % to corresponding (wild-type or REDD1 KO) control ear weight. The means±SD were calculated for six individual ear punches/condition in one representative experiment (out of three experiments). Statistical analysis for differences between treatment and corresponding control was done by the unpaired two-tailed t-test.

To further assess the consequences of REDD1 knockout for glucocorticoid therapy, we measured their responses to FA in a model where inflammation/edema is induced by topical irritant croton oil (CO) in the mouse ear. This assay is typically employed to test anti-inflammatory effects of GR ligands (Schäcke et al, 2004; Park et al, 2006; Schoepe et al, 2010). REDD1 KO animals and isogenic controls were equally responsive to inflammation (FIG. 5). Remarkably, FA relieved this inflammatory response with equal potency in wild-type and REDD1 KO mice as assessed by changes in ear morphology and the weight of ear punch (FIG. 5).

REDD1 Knockdown Reduces Hypoplastic Effect of Glucocorticoids in Organotypic Raft Cultures.

Figure 6:
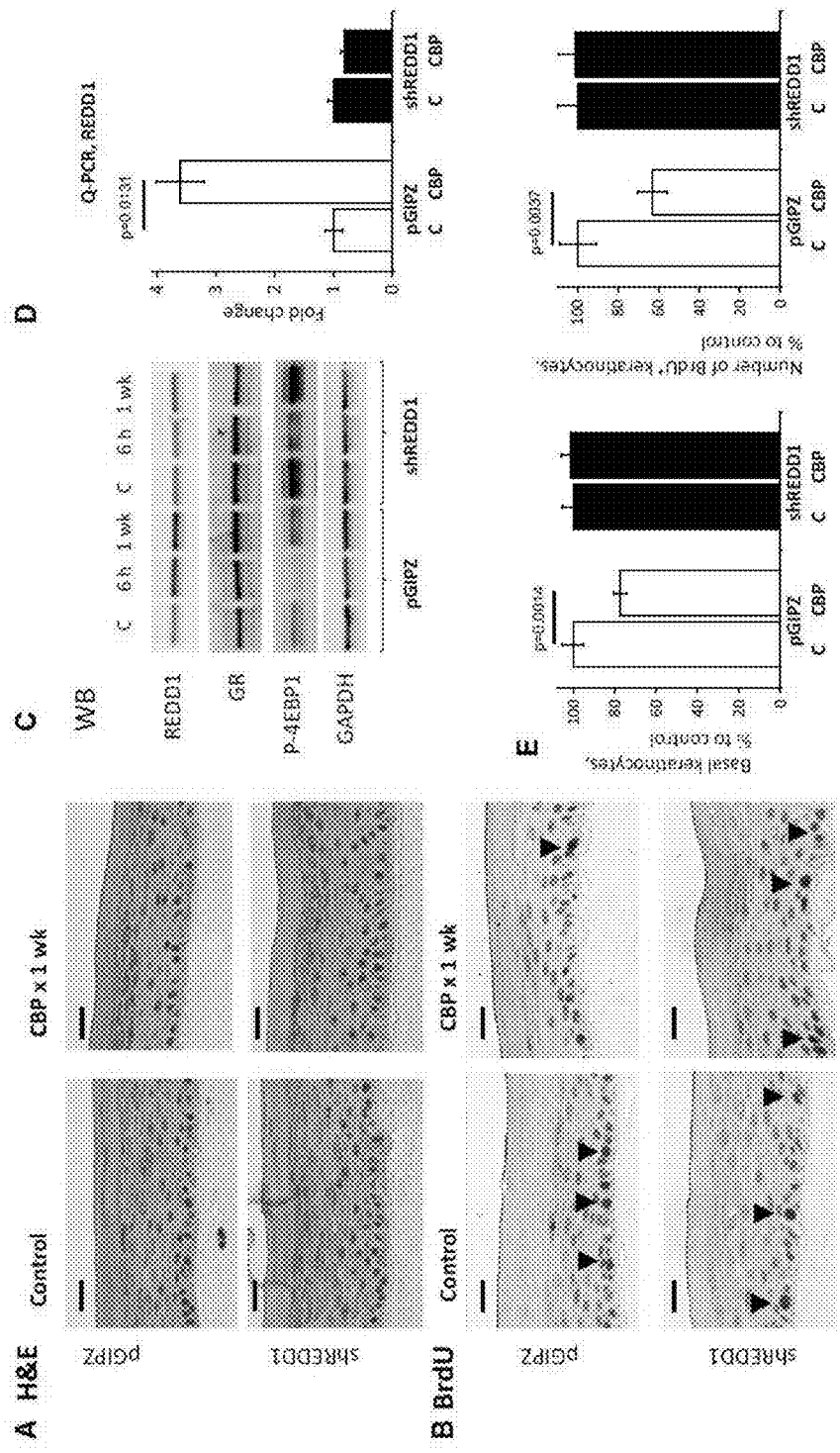
FIG. 6. Down-regulation of REDD1 protects organotypic raft cultures from the hypoplastic effect of glucocorticoids. Organotypic raft cultures (ORC) made from NHEK infected with REDD1 shRNA and control pGIPZ lentiviruses were treated with glucocorticoid CBP (5 µM) or vehicle control (0.05% DMSO) for 7 days. A, B. H&E and BrdU staining of raft cultures (BrdU$^+$ cells are indicated by arrowheads). Scale bars are 10 µm. C. Western blot analysis of REDD1, GR, and mTOR substrate 4E-BP1 phosphorylation. GAPDH was used as a loading control. D Q-PCR analysis of REDD1 expression in rafts. E. Analysis of CBP effect on basal keratinocyte number (left) and keratinocyte proliferation (number of BrdU$^+$ basal keratinocytes/total number of basal keratinocytes, right) is presented as % to corresponding control rafts. Data information: The means±SD for BrdU$^+$ cells and basal keratinocytes in (E) were calculated for two individual rafts in one representative experiment (20 measurements/condition) out of two experiments. Q-PCR results in (D) are the means±SD calculated for two individual RNA samples/condition. Statistical analysis for differences between treatment and control was done by the unpaired two-tailed t-test.

To evaluate possible contribution of REDD1 to glucocorticoids' action in human skin, we used 3-dimensional organotypic raft cultures (ORC) made of primary human epidermal keratinocytes (NHEK, Getsios et al, 2009) as described previously (Schoepe et al, 2010). We prepared ORCs from NHEK infected with control pGIPZ- or shREDD1-expressing lentiviruses (FIG. 6A). Both short-term (6 h) and chronic (7 days) treatment with CBP induced REDD1 mRNA and protein in control ORCs; this induction was completely abolished in shREDD1 ORCs (FIGS. 5C, D). In agreement, mTOR activity was increased in shREDD1-expressing rafts compared to pGIPZ controls, with or without CBP treatment, as was evidenced by increased 4E-BP1 phosphorylation (FIG. 6C).

In pGIPZ-infected ORCs, the number and especially proliferation (BrdU incorporation) of basal keratinocytes were decreased by 25-40% after 7-day treatment with CBP (FIGS. 6A, B, E). In contrast, shREDD1-expressing ORCs were completely protected from the hypoplastic/anti-proliferative effect of CBP (FIGS. 6A, B, E).

REDD1 Plays an Important Role in GR Signaling: Asymmetrical Effect on GR TA and TR.

The reduced sensitivity of REDD1 KO mice and shREDD1 ORCs to steroid-induced atrophy suggested that lack of REDD1 could affect either GR expression or GR function. Q-PCR and Western blotting showed that GR expression was not significantly changed/slightly increased either in the epidermis of REDD1 KO mice (FIG. 4D) or in ORCs after shREDD1 knockdown (FIG. 6C).

To investigate the global role of REDD1 in GR signaling, we performed genome-wide expression profiling of the epidermis of REDD1 and wild-type mice treated with vehicle (control) or FA using Illumina mouse whole-genome gene array (GEO Submission GSE59151). Gene expression was measured 24 h post-FA application, when both TA and TR are usually fully developed (Wu et al, 2004). Differential expression was identified based on the adjusted P-value threshold of 0.05.

REDD1 KO had only minor effect on baseline gene expression with only three genes were up-regulated and 23 were down-regulated in REDD1 KO compared to wild-type controls (data not shown, see Baida et al., EMBO, 2015, at Supplementary Table S1, and heatmaps FIG. 7A and Supplementary FIG. S4).

In contrast, REDD1 appeared central for gene regulation by glucocorticoids. In REDD1 KO animals, ~20% fewer genes responded to FA than in wild-type mice: (338 versus 397 up-regulated and 337 versus 441 down-regulated, (data not shown, see Baida et al., EMBO, 2015, at FIG. 7B and Supplementary Table S2). More importantly, the lack of REDD1 specifically altered TA branch of GR signaling. Only 30% FA-induced genes were also activated in REDD1 KO mice. In contrast, there was a 50% overlap between genes inhibited by FA in REDD1 KO and wild-type animals (data not shown, see Baida et al., EMBO, 2015, at FIG. 7B and a detailed analysis of differentially regulated individual genes in two genotypes in Supplementary Table S2).

To quantify the relationship between TA and TR and REDD1 gene status, we assessed Pearson correlation between the fold changes of the differentially expressed (397 activated and 441 down-regulated) genes in wild-type and in REDD1 KO epidermis. We found only a weak positive correlation between FA-induced genes (r=0.16, P=0.003), and a robust positive correlation between FA-inhibited genes (r=0.72, P=10e−10), indicating much stronger involvement of REDD1 in GR TA, but not TR. This conclusion is also illustrated by the hierarchical clustering of microarray data on the heatmap with high level of similarity between genes repressed by FA in wild-type and REDD1 KO animals (data not shown, see Baida et al., EMBO, 2015, at FIG. 7A, Supplementary FIG. S4).

Next, we performed Gene Ontology (GO) enrichment analysis of the differentially expressed genes for each comparison (see Tables 1, 2, 3, and 4, illustrating enriched Gene Ontology (GO) categories, fold enrichment cutoff≥3.0, P<0.01).

TABLE 1 w.t.: FA vs control, up-regulated genes

| Term | P-value | Fold Enrichment |
|---|---|---|
| GO:0006665~sphingolipid metabolic process | 3.85E−04 | 5.87 |
| GO:0006643~membrane lipid metabolic process | 4.77E−04 | 5.67 |
| GO:0004091~carboxylesterase activity | 8.59E−04 | 4.48 |
| GO:0006672~ceramide metabolic process | 1.17E−03 | 7.39 |
| GO:0046519~sphingoid metabolic process | 1.52E−03 | 6.98 |
| GO:0006644~phospholipid metabolic process | 3.28E−03 | 3.05 |
| GO:0016765~transferase activity, transferring alkyl or aryl (other than methyl) groups | 3.75E−03 | 5.71 |
| GO:0046479~glycosphingolipid catabolic process | 5.39E−03 | 25.11 |
| GO:0005885~Arp2/3 protein complex | 5.75E−03 | 24.28 |

TABLE 2

REDD1 KO: FA vs control, up-regulated genes

| Term | P-value | Fold Enrichment |
|---|---|---|
| GO:0005776~autophagic vacuole | 4.99E−04 | 23.64 |
| GO:0051270~regulation of cell motion | 5.20E−03 | 3.78 |
| GO:0042598~vesicular fraction | 5.84E−03 | 3.02 |
| GO:0005770~late endosome | 6.43E−03 | 6.65 |
| GO:0008440~inositol trisphosphate 3-kinase activity | 8.09E−03 | 20.98 |
| GO:0030334~regulation of cell migration | 9.17E−03 | 3.88 |

TABLE 3 w.t.: FA vs control, down-regulated genes

| Term | P-value | Fold Enrichment |
|---|---|---|
| GO:0006260~DNA replication | 1.35E−06 | 4.72 |
| GO:0002495~antigen processing and presentation of peptide antigen via MHC class II | 3.00E−05 | 15.11 |
| GO:0019886~antigen processing and presentation of exogenous peptide antigen via MHC class II | 3.00E−05 | 15.11 |
| GO:0042613~MHC class II protein complex | 4.99E−05 | 21.39 |
| GO:0002504~antigen processing and presentation of peptide or polysaccharide antigen via MHC class II | 5.91E−05 | 13.33 |
| GO:0002478~antigen processing and presentation of exogenous peptide antigen | 2.26E−04 | 10.30 |
| GO:0019882~antigen processing and presentation | 3.27E−04 | 5.15 |
| GO:0005773~vacuole | 4.65E−04 | 3.01 |
| GO:0019884~antigen processing and presentation of exogenous antigen | 6.21E−04 | 8.39 |
| GO:0048002~antigen processing and presentation of peptide antigen | 1.39E−03 | 7.08 |

TABLE 3-continued w.t.: FA vs control, down-regulated genes

| Term | P-value | Fold Enrichment |
|---|---|---|
| GO:0042287~MHC protein binding | 1.87E−03 | 15.19 |
| GO:0030145~manganese ion binding | 2.35E−03 | 3.19 |
| GO:0005657~replication fork | 3.10E−03 | 8.02 |
| GO:0042611~MHC protein complex | 3.51E−03 | 5.78 |
| GO:0005663~DNA replication factor C complex | 3.87E−03 | 28.88 |

TABLE 4

REDD1 KO: FA vs control, down-regulated genes

| Term | P-value | Fold Enrichment |
|---|---|---|
| GO:0002495~antigen processing and presentation of peptide antigen via MHC class II | 8.11E−06 | 19.77 |
| GO:0019886~antigen processing and presentation of exogenous peptide antigen via MHC class II | 8.11E−06 | 19.77 |
| GO:0003735~structural constituent of ribosome | 1.44E−05 | 4.85 |
| GO:0002504~antigen processing and presentation of peptide or polysaccharide antigen via MHC class II | 1.62E−05 | 17.45 |
| GO:0042613~MHC class II protein complex | 2.74E−05 | 24.92 |
| GO:0002478~antigen processing and presentation of exogenous peptide antigen | 6.34E−05 | 13.48 |
| GO:0019884~antigen processing and presentation of exogenous antigen | 1.79E−04 | 10.98 |
| GO:0006631~fatty acid metabolic process | 1.98E−04 | 3.71 |
| GO:0019882~antigen processing and presentation | 3.50E−04 | 5.99 |
| GO:0005840~ribosome | 3.64E−04 | 3.47 |
| GO:0048037~cofactor binding | 3.70E−04 | 3.26 |
| GO:0048002~antigen processing and presentation of peptide antigen | 4.11E−04 | 9.27 |
| GO:0033559~unsaturated fatty acid metabolic process | 5.50E−04 | 8.72 |
| GO:0042287~MHC protein binding | 9.42E−04 | 19.26 |
| GO:0016126~sterol biosynthetic process | 1.70E−03 | 9.51 |
| GO:0042611~MHC protein complex | 1.81E−03 | 6.73 |

Figure 7:
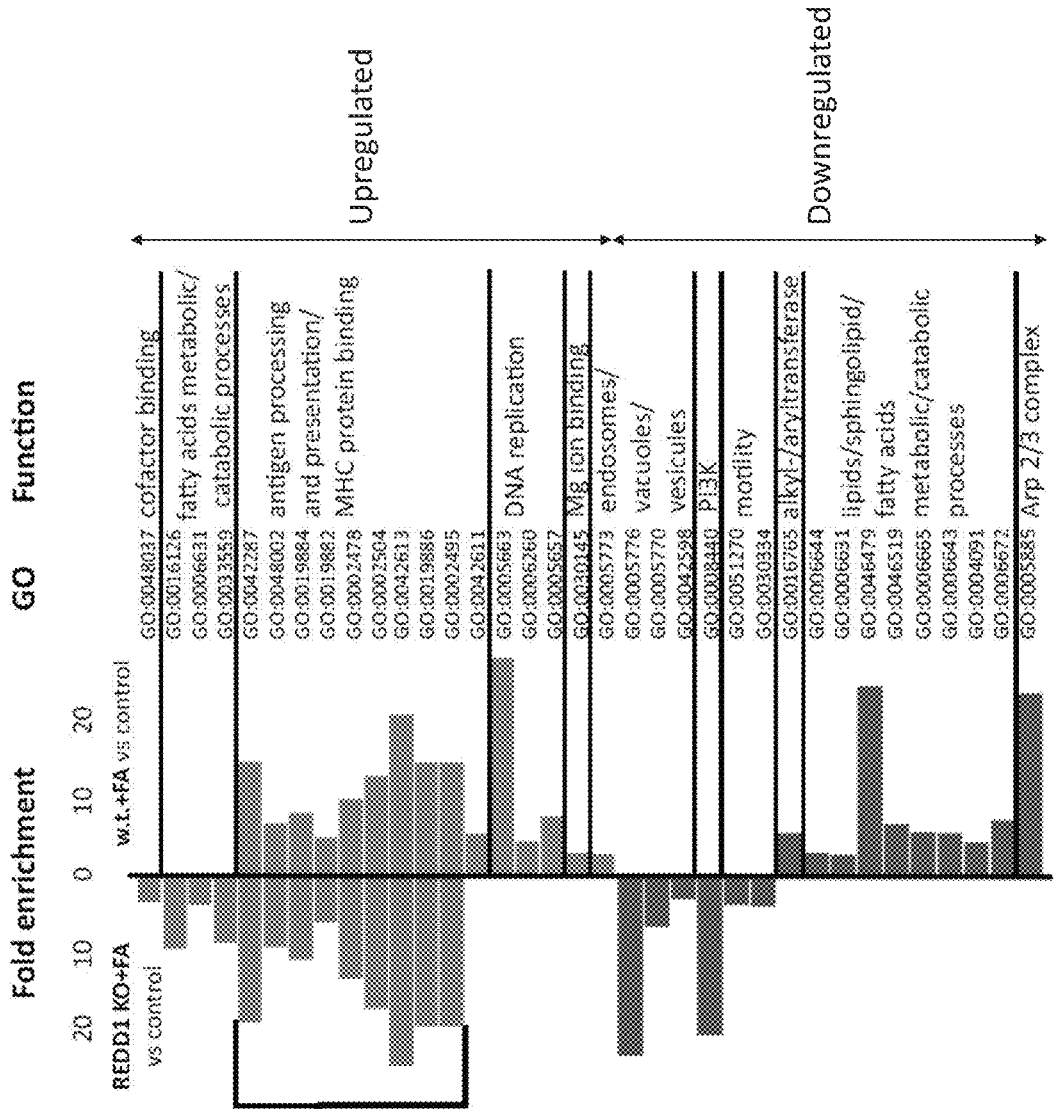
FIG. 7. Global effect of REDD1 KO on the expression of glucocorticoid-responsive genes in murine epidermis. REDD1 KO and isogenic B6×129 mice were treated topically with FA (2 µg) or vehicle (acetone) for 24 h, and RNA was extracted from the epidermis and used for microarray analysis. Most enriched gene ontology (GO) categories for biological processes and molecular functions (fold-change enrichment≥3, P<0.01), associated with transrepression and transactivation of the glucocorticoid-responsive genes in REDD1 KO and wild-type mice. A lack of overlap in GO categories between KO and wild-type mice associated with up-regulated genes and significant overlap in the function of down-regulated genes was observed. Data information: For array analysis, we used two individual RNA samples/condition. Statistical analysis of DNA arrays is described in Materials and Methods. Statistical analysis of array validation also was performed. (Data not shown, see Baida et al., EMBO, 2015, at Supplementary FIG. S3.

The most enriched GO terms associated with the up-regulated genes in wild-type epidermis included metabolic processes (lipids, sphingolipids, and fatty acids), catabolism (lipids, sphingolipids, proteins), and proteolysis. These metabolic and catabolic gene categories were absent among genes up-regulated in REDD1 KO epidermis (FIG. 7). Instead, in REDD1 KO keratinocytes, FA up-regulated genes related to autophagy, endosomes, and PI3K signaling. Remarkably, the GO analysis of gene repression showed 70% overlap between REDD1 KO and wild-type animal response, with predominant categories related to the anti-inflammatory effect of glucocorticoids (antigen processing/presentation, and MHC/major histocompatibility complex protein binding) (FIG. 7). In addition, FA inhibited genes related to DNA replication, reflective of the anti-proliferative effect of glucocorticoids in wild-type but not in REDD1 KO skin.

Array validation was performed by Q-PCR for six genes from different GO categories, inhibited (Cd74, H2-Ab1) or up-regulated (Fkbp5, Elovl3, Rptn, Socs2) by FA in wild-type epidermis (data not shown, see Baida et al., EMBO, 2015, at FIG. 7D). Remarkably, Cd74 and H2-Ab1 associated with class II MHC and important for antigen presentation and immune response (Pan et al, 2001; Beswick & Reyes, 2009) were similarly down-regulated in wild-type and in REDD1 KO epidermis (data not shown, see Baida et al., EMBO, 2015, at FIG. 7D). The examples of genes differentially activated in wild-type and REDD1 KO epidermis include Elovl3 involved in lipid metabolism (Guillou et al, 2010), Rptn, a multifunctional matrix protein (De Guzman Strong et al, 2010), Socs2, which regulates cell signaling and protein degradation (Larsen & Ropke, 2002), and Fkbp5, a molecular chaperone involved in steroid receptor activation, and also an inhibitor of mTOR and Akt (Li et al, 2011; Vandevyver et al, 2012) (data not shown, see Baida et al., EMBO, 2015, at FIG. 7D). Q-PCR data for all these genes were in perfect agreement with the DNA array analyses (Pierson correlation>0.9, (data not shown, see Baida et al., EMBO, 2015, at Supplementary FIG. S3).

Overall, the analysis of gene expression at single gene and GO category levels, for the first time, revealed a feed-forward loop whereby GR target REDD1 is necessary for its TA action.

REDD1 does not alter GR phosphorylation and nuclear localization. The major steps required for GR-dependent TA are phosphorylation and nuclear translocation. ORC are notoriously difficult for biochemical analyses using multiple time points. Thus, we used immortalized human keratinocytes (HaCaT), stably infected with control pGIPZ or shREDD1 lentiviruses, in which shREDD1 prevented REDD1 activation by glucocorticoid FA (FIG. 8A).

Figure 8:
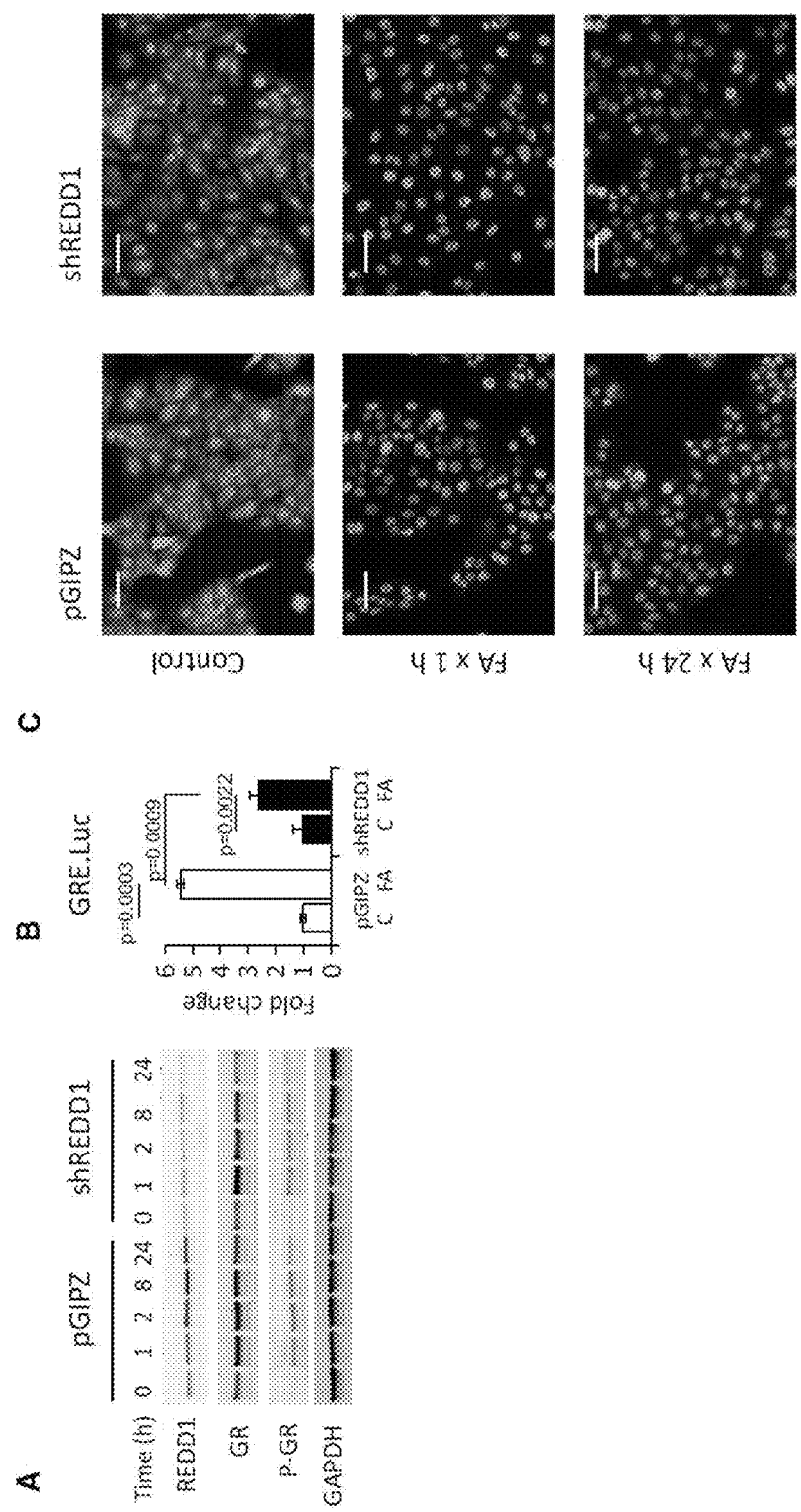
FIG. 8. REDD1 inhibition did not affect GR phosphorylation and nuclear translocation in HaCaT human keratinocytes. HaCaT human keratinocytes were infected with shREDD1 or pGIPZ (control) lentiviruses and treated with glucocorticoid FA ($10^{-6}$ M) for the indicated time. Western blot analysis of REDD1, GR, and phosphorylated GR-Ser211. GAPDH used as a loading control. Reduced induction of Luciferase reporter in shREDD1-HaCaT cells. shREDD1- and pGIPZ-HaCaT cells were infected with GRE.Luc lentivirus and treated with FA ($10^{-6}$ M) for 24 h. The Luciferase induction is presented as a fold change to corresponding vehicle-treated control. The means±SD were calculated for three individual wells/group in one representative experiment (out of three experiments). Statistical analysis for differences between groups was done by ANOVA Immunofluorescence analysis of GR nuclear translocation and retention in shREDD1- and pGIPZ-HaCaT cells treated with FA ($10^{-6}$ M). Scale bars are 10 µm.

In agreement with the impaired activation of GR target genes in REDD1 KO animals, GR activation was strongly decreased by REDD1 knockdown in HaCaT keratinocytes as assessed by Luciferase assay with GRE.Luciferase reporter (FIG. 8B). Upon ligand binding, GR is typically degraded; however, in some cells, this degradation is minimal and may be preceded by temporary GR accumulation (Yemelyanov et al, 2008). We observed this temporary GR accumulation in HaCaT cells (FIG. 8A). Despite the difference in GR activity in Luciferase assay, basal GR levels, the dynamics of GR protein changes, GR phosphorylation, and nuclear translocation in response to FA were identical in shREDD1- and pGIPZ-HaCaT keratinocytes (FIGS. 8A, C).

Similar Mechanisms Control Skin and Muscle Atrophy.

Glucocorticoids can induce catabolic/atrophic changes in multiple tissues including muscle, subcutaneous fat, and bone (Wang et al, 2006; Shimizu et al, 2011). We used ProfileChaser software to compare transcriptional responses to glucocorticoids in epidermis and other tissues, using our array data and DNA arrays deposited to NCBI (Engreitz et al, 2010; Dudley et al, 2011). The comparison revealed remarkably high degree of similarity between gene expression patterns in steroid responses of the epidermis and muscle and, unexpectedly, steroid-independent changes in Duchene muscular dystrophy (similarity scores 0.66 and 0.64 accordingly, Tables 1, 2, 3, and 4).

Discussion

This work represents comprehensive investigation of the mechanisms of adverse and therapeutic glucocorticoid effects in skin, which combines focused and global, genome-wide methods of analysis.

First, we shed new light on the dynamics of molecular responses to topical glucocorticoids in the skin. We have identified REDD1 as an early glucocorticoid-responsive gene in mammalian skin. REDD1 activation in mice occurs 4-8 h after the treatment when it inhibits mTOR and promotes autophagy in the epidermis. Later, at the end of 2-week glucocorticoid treatment, both REDD1 and mTOR activity return to basal levels (FIG. 2B). This is the time point when mice develop resistance to topical glucocorticoids (tachyphylaxis) (Chebotaev et al, 2007c). In contrast to mice, tachyphylaxis does not occur in patients (Taheri et al, 2013); this could be possibly caused by persistence of REDD1 up-regulation.

This is the first study in which REDD1 KO mice were used to determine the contribution of REDD1 to skin maintenance and response to glucocorticoids. In general, REDD1 role in skin and keratinocytes has not been studied; a single report suggests increased keratinocyte differentiation in vitro due to REDD1 (Ellisen et al, 2002). In our study, REDD1 had minimal effect on the gene expression in adult epidermis, and this is corroborated by the fact that adult REDD1 KO animals have no overt skin phenotype, likely due to low basal REDD1 levels.

At the same time, REDD1 induction by glucocorticoids was critically important for skin atrophy. In REDD1 KO mice, all skin compartments were protected from the atrophogenic effect of steroids. Likewise, ORCs of human epidermis, which are currently the most advanced model of human skin (Getsios et al, 2009; Schoepe et al, 2010), were also protected from hypoplasia by REDD1 knockdown. In contrast to its central role in adverse cutaneous effects of steroids, REDD1 is dispensable for the anti-inflammatory effect of glucocorticoids as FA alleviated inflammation and edema due to croton oil in both REDD1 KO and control mice.

Interestingly, REDD1 knockout safeguarded at least two populations of stem cells: CD34+ follicular epithelial stem cells and p63+ keratinocyte progenitors from the detrimental effects of glucocorticoids. These data along with recent observations that REDD1 is decreased during reprogramming of somatic cells to induced pluripotent stem cells (Corominas-Faja et al, 2013) suggest an important role for REDD1 in stem cells maintenance. CD34 is also a marker of white adipose stem cells (Park et al, 2008), and thus, protection of CD34+ adipocytes could explain the observed protection of s.c. fat in REDD1 KOs.

Recent report documents the inhibitory effect of mTOR on GR function in the muscle (Shimizu et al, 2011); however, the effect of REDD1 and other mTOR inhibitors on GR signaling has not been well studied. Our bioinformatics analysis of transcriptional response to glucocorticoids in the skin identified a novel intriguing role of REDD1 in control of the repertoire of glucocorticoid-regulated genes and the integral functional response to glucocorticoids. Furthermore, the lack of REDD1 predominantly affected gene activation (TA) and not inhibition (TR) by glucocorticoids.

While TA involves binding of GR homodimers to palindromic GREs in the promoters and enhancers of the glucocorticoid-inducible genes, TR is largely independent of GR dimerization and in many cases stems from the direct interaction (tethering) between GR monomer and another transcription factors including pro-inflammatory NF-kB and AP-1. Another TR mechanism is binding of GR monomers to 'negative GREs' (Nixon et al, 2013; Ratman et al, 2013). The TA versus TR outcome also depends on the recruitment of steroid hormone receptor coactivators (such as SRC-1, SRC2) and corepressors (such as NCoR, SMRT) (Ratman et al, 2013). As GR phosphorylation and nuclear import/retention were similar in control and shREDD1-HaCaT keratinocytes, it is conceivable that REDD1 modifies conditions for GR dimerization and DNA binding, or impinges on the specter of coregulators recruited by GR.

TR by GR is critical for its anti-inflammatory function, even though the induction of select GR-dependent genes is also needed (Schäcke et al, 2006, 2009; Chebotaev et al, 2007a; Clark et al, 2008; Ratman et al, 2013). In contrast, many side effects of GR are caused by its TA action (Schäcke et al, 2006, 2009; Ratman et al, 2013). Thus, selective GR activators (SEGRA) that shift GR activity toward TR are expected to have a better therapeutic profile than classical glucocorticoids. Indeed, several SEGRA including ZK245186/mapracorat preserve the anti-inflammatory effect of glucocorticoids but do not induce skin atrophy (Schäcke et al, 2009). We demonstrate that REDD1 deletion 'dissociates' TA and TR functions of glucocorticoids.

Chronic glucocorticoid therapy induces atrophy in many organs besides skin (Wang et al, 2006; Shimizu et al, 2011; Henneicke et al, 2014). Meta-analysis of ours and published gene arrays revealed strong similarity between changes in transcriptome in glucocorticoid-treated epidermis (our results) and muscle undergoing steroid-dependent and steroid-independent (Duchene atrophy) waste. Thus, molecular mechanisms underlying the atrophy in epidermis and muscle are likely similar and involve REDD1. We also speculate that similar REDD1-dependent mechanisms underlie the steroid atrophy of s.c. adipose as REDD1 was highly induced in s.c. adipocytes, and s.c. fat was protected in REDD1 KO mice from glucocorticoids.

In conclusion, we discovered that REDD1 acts as GR modulator and atrophogen in the skin. Further, our results suggest the clinical relevance of REDD1 as molecular target for safer combination GR-targeted therapies in the skin. We expect that blocking REDD1 by pharmacological inhibitors or RNAi could reduce and possibly alleviate skin atrophy in response to steroids; this is a new strategy for safer glucocorticoid treatments of chronic inflammatory diseases in the skin and other tissues.

Materials and Methods

Chemicals.

Fluocinolone acetonide (FA), croton oil (CO), and all other chemicals unless stated otherwise were purchased from Sigma-Aldrich Corp. (St. Louis, Mo., USA). Clobetasol propionate (CBP) was purchased at the pharmacy as 0.05% cream.

Animals and Treatments.

B6D2 (F1 C57Bl×DBA) mice used previously to study steroid skin atrophy (Chebotaev et al, 2007c) were obtained from Jackson Laboratory (Bar Harbor, Me., USA). REDD1 KO mice in F1 C57BL/6×129SvEv genetic background (B6×129) were generated by Lexicon Genetics Inc. for Quark Pharmaceuticals Inc. REDD1 exon 2 was replaced with LacZ/neo expression cassette (Brafman et al, 2004). Wild-type B6×129 isogenic control females were obtained from Taconic (Germantown, N.Y., USA).

Seven-week-old females in the telogen stage of the hair cycle were shaved and treated 3 days later. Glucocorticoid FA was applied topically (2 μg/animal) in 200 μl acetone to the back skin once or up to four times every third day as described (Chebotaev et al, 2007c). Control animals were treated with acetone only. Skin was harvested 4-24 h after FA application as indicated in Figure legends. Animals were injected i.p. with bromodeoxyuridine (BrdU, Sigma-Aldrich, 50 μg/g of animal weight) 1 h before skin was harvested. Epidermis and s.c. fat were isolated from the murine dorsal skin mechanically by scraping (Chebotaev et al, 2007c).

In our work with animals, we adhered to ACUC protocols approved by the Northwestern University Animal Care and Use Committee. The protocols specify experimental procedures (topical treatment with glucocorticoids, ear edema test, BrdU injections), mouse strains (C57Bl×129; C57Bl× DBA, REDD1 KO), animal sex (males and females), age (from 5 weeks to 1 year), number of animals allowed to use, housing details (five animals/cage, regular chow diet, food and water ad libitum, 12 h on/12 h off light exposure), and animal euthanasia. All animals were maintained at the Northwestern University barrier animal facility.

Ear Edema Test.

To evaluate the anti-inflammatory effect of glucocorticoid FA, we used ear edema test (Schäcke et al, 2004; Park et al, 2006; Schoepe et al, 2010). Seven-week-old female animals were pretreated with FA (2 μg in 20 μl of acetone) or vehicle (20 μl of acetone) applied to the back of the ear lobe 1 h before application of nonspecific contact irritant croton oil (CO, 10% solution in 20 μl of acetone). Mice were sacrificed and ears were harvested 9 h after CO application, the time point at which we observed maximum ear edema in B6×129 animals (data not shown). Four-millimeter ear punch biopsies were immediately weighted to assess ear edema. In all experiments, we used 3-4 animals/group; experiments were repeated 2-3 times.

Treatment of Human Volunteers.

Glucocorticoid CBP was applied topically as a 0.05% cream to the skin of right arm of healthy human volunteers (age 32-65) once or every 24 h for 2 weeks. Untreated left arm skin was used as control. Four-millimeter-full-thickness punch skin biopsies were taken 24 h after the last CBP application as indicated in Figure legends. Whole human skin samples were used for the molecular biological studies.

Keratinocyte Cell Lines and 3-D Organotypic Raft Cultures.

Three-dimensional (3-D) organotypic raft cultures (ORC) of human epidermis were made as described in Getsios et al (2009). Briefly, neonatal human epidermal keratinocytes (NHEK) were infected with shRNA- and pGIPZ-expressing lentiviruses followed, 48 h later, by selection for puromycin (2 μg/ml) resistance. Selected keratinocyte cultures were reseeded onto collagen gels with embedded J2-3T3 fibroblasts and cultured at the air-liquid interface as previously described for 3 days to allow the initial phase of epidermis formation. The standard ORC medium contains high $5 \times 10^{-7}$ M hydrocortisone. In our experiments, ORC were cultured in the medium with $10^{-8}$ M hydrocortisone during first 3 days and then were treated with glucocorticoid CBP ($5 \times 10^{-6}$ M) or vehicle control (0.05% DMSO) for 7 days. Rafts were treated with BrdU ($10^{-7}$ M) 1 h before harvesting and fixed in formalin. The epithelial sheets were peeled off the collagen lattice, snap-frozen, protein and RNA extracted, and processed for Western blot analysis and Q-PCR.

HaCaT human keratinocyte cell line is an in vitro spontaneously transformed keratinocytes from histologically normal skin. Line was established by Dr. Fusenig (Boukamp et al, 1988). We have obtained HaCaT cells from Dr. M Denning (Loyola University, Chicago, Ill.) who received them directly from Dr. Fusenig. It is known that HaCaTs express basal keratin K14 and can express keratins K1/K10 when induced to differentiate by high Ca2+ (Boukamp et al, 1988). We confirmed that our subline of HaCaT cells express keratinocyte differentiation markers using Q-PCR (data not shown). Cells were cultured in Dulbecco's modified Eagle's medium (DMEM, Cellgro, Manassas, Va., USA) containing 10% PBS (Cellgro) and antibiotics.

Lentiviruses: shREDD1-Lentiviral Construct.

To knockdown REDD1 expression in keratinocytes, we used lentiviral construct expressing shREDD1 targeting REDD1 3' UTR sequences homologous in human and mouse (clone V2LHS_176476, Thermo Scientific GIPZ Lentiviral shRNA Library). Empty pGIPZ vector (Open Biosystems, GE Healthcare Bio-Sciences, Pittsburgh, Pa., USA) was used as a control.

Lentiviruses: GRE.Luciferase Reporter.

GRE.Luc reporter lentiviral construct encoding Firefly Luciferase under transcriptional regulation of glucocorticoid-responsive elements and a control lentiviral construct with Firefly Luciferase under minimal CMV promoter (used as control) were obtained from DNA/RNA delivery Core, SDRC Northwestern University. Lentiviral stocks, packaging, and transduction procedures were performed as described in Zufferey et al (1998) and Yemelyanov et al (2007).

Luciferase Assay.

HaCat cells expressing Firefly Luciferase under minimal CMV promoter or promoter containing GRE were plated in 12-well plates (three wells/experimental group), grown to ~60% and treated with FA or vehicle (0.01% DMSO) for 24 h. Luciferase activity was measured using commercial Luciferase Assay (Promega Corp., Madison, Wis., USA) and Luminometer TD 20/20 (Turner Designs, Sunnyvale, Calif., USA). Luciferase activity of GRE.Luc construct was normalized to Luciferase activity from minimal CMV promoter under the same experimental condition.

Histological Analysis and Immunostaining.

Sections of formalin-fixed, paraffin-embedded skin and ORCs were stained with hematoxylin and eosin (H&E), Masson's trichrome to evaluate the effect on dermis and collagen fibers (Sheehan & Hrapchack, 1980), and with antibodies against BrdU (BD Biosciences, San Jose, Calif., USA), keratins 1, 5, and 10, loricrin (Covance, Princeton, N.J.), phospho-mTORSer2448 (Cell Signaling Technology, Inc., Danvers, Mass., USA), REDD1 (Proteintech Group, Inc, Chicago, Ill.), p63 (eBioscience, San Diego, Calif., USA), and CD34 (Abcam, Cambridge, Mass., USA).

GR nuclear translocation was determined by immunofluorescence in HaCaT cells. Cells infected with pGIPZ and shREDD1 lentiviruses were selected with puromycin, seeded on coverslips. After the treatments, cells were fixed with 2% formaldehyde and permeabilized with acetone:methanol (1:1 v/v). After blocking, cells were incubated with primary rabbit anti-GR antibody (H-300, Santa Cruz Biotechnology, Santa Cruz, Calif., USA) followed by secondary anti-rabbit FITC-conjugated antibody (Jackson Immuno Research). Cell nuclei were counterstained with DAPI (Invitrogen, Life Technologies, Grand Island, N.Y., USA). Cell and tissue images were taken with AxioCaM HRC camera linked with Zeiss Axioplan2 microscope.

Morphometric Analysis.

Quantification of the epidermal width and number of basal keratinocytes (as the readouts for skin atrophy and hypoplasia of raft epidermis) was performed in dorsal skin and ORC sections stained with H&E. The number of dermal cells was determined on sections stained with Masson's trichrome in the upper (papillary) dermis that is distinguishable from the lower (reticular) dermis (Driskell et al, 2013). At least 10 individual fields per slide with at least three samples in each experimental group were counted using Axioplan2 microscope software (Carl Zeiss). All measurements are presented as % to corresponding control.

The numbers of BrdU+, p63+, and total number of basal keratinocytes were evaluated in 10 fields of view in each skin/ORC sample under the microscope. Number of BrdU+ and p63+ cells is presented as percent of total number of basal keratinocytes. The number of CD34+ hair follicles among 10 randomly selected hair follicles per skin sample was evaluated under the microscope.

Western Blot Analysis.

The whole-cell protein extracts were prepared using RIPA buffer with protease and phosphatase inhibitor cocktails (Thermo Scientific, Thermo Fisher Scientific Inc., Waltham, Mass., USA), resolved by SDS-PAGE on 4-20% gels and transferred to Odyssey nitrocellulose membranes (LI-COR Biosciences, Lincoln, Neb., USA). Membranes were blocked with Odyssey Blocking Buffer and incubated with primary antibodies overnight at 4° C., followed by IRDye® secondary antibodies (LI-COR Biosciences). LI-COR Odyssey Imager was used for the band visualization. Equal loading and adequate transfer to the membranes were verified by staining with Ponceau S (Sigma-Aldrich) and with anti-GAPDH (Sigma-Aldrich) antibody. We used Abs against: REDD1 (Proteintech Group, Inc., Chicago, Ill.), LC3B, phospho-rpS6Ser240/244, phospho-4E-BP1Thr37/46, phospho-GRSer211 (Cell Signaling Technology, Inc.), and GR (H-300 or M-20, Santa Cruz Biotechnology, Inc.).

Abs against REDD1 and Beclin-1 (FIG. 2B, C) were reported to recognize multiband pattern on Western blots (Katiyar et al, 2009; Li et al, 2012; Regazzetti et al, 2012, which may reflect phosphorylation status of these proteins.

RNA Isolation and Quantitative and Semi-Quantitative RT-PCR.

Total RNA from murine epidermis, whole human skin, and cell cultures was isolated with RiboPure kit (Ambion, Life Technologies, Grand Island, N.Y., USA). Total RNA from murine s.c. adipose was isolated with RNeasy Lipid Tissue Kit (Qiagen, Valencia, Calif., USA). The RNA samples were treated with TURBOT™ DNase (Ambion). The gene expression was assessed using semi-quantitative two-step RT-PCR and quantitative Q-PCR. Reverse transcription was performed using 1 µg RNA, random hexamers, and M-MLV reverse transcriptase (Invitrogen, Life Technologies), according to manufacturer instructions. The gene-specific primers were designed with NCBI Primer-BLAST (data not shown, see Baida et al., EMBO, 2015, at Supplementary Table S4). Q-PCR with SYBR Green detection was performed on the Applied Biosystems® 7000 Real-Time PCR instrument (Life Technologies). Each sample was tested in triplicate, and results were normalized to the expression of the housekeeping Rp127 gene (de longe et al, 2007). For semi-quantitative PCRs, Taq DNA polymerase (Promega) was used, and PCR products were separated on 1.5% agarose gel and visualized using automated imaging system (Bio-Rad, Hercules, Calif., USA). RPL27 was used as a normalization control.

Microarray Analysis of Gene Expression.

RNA samples were checked for quality and integrity with the Agilent 2100 bioanalyzer and used for microarray analysis. RNA amplification, labeling, and hybridization with the Mouse Whole-Genome Gene Expression BeadChips MouseRef-8 v2.0 (Illumina) were performed at the Genomics Core Facility at the Center for Genetic Medicine at Northwestern University according to Illumina protocols.

Microarray processing was performed using the Limma package (Smyth, 2005), using the neqc function to perform background subtraction using the negative control probes, and quantile normalization using both positive and negative control probes. Differentially expressed probes were identified using the linear model implemented in Limma, applying an adjusted P-value threshold of 0.05. Q-PCR and microarray based gene expression values were compared using linear Pearson correlation.

FA-Induced Transactivation and Transrepression.

To quantify the relationship between FA-induced transactivation and transrepression across both phenotypes, we correlated the fold change of the differentially expressed probesets in wild-type, with their corresponding values in REDD1 KO epidermis.

Gene Ontology and Pathway Analysis.

Gene ontology analysis was performed using the DAVID Bioinformatics resource tool (Huang et al, 2009a,b), submitting differentially expressed probes from each experiment, against the probe background of MouseRef 8. DAVID performs a hypergeometric test to identify overrepresented GO terms in a list of differentially expressed probes. Results are presented for categories with greater than or equal to threefold enrichment and P=0.01.

Gene Expression Heatmaps.

Heatmaps were generated using differentially expressed probesets (adjusted P=0.05) induced by the application of FA, for the REDD1 KO and wild-type isogenic mice. Samples and genes were hierarchically clustered according to the Euclidean distance of the normalized gene expression values, and clusters were merged using complete linkage. Heatmaps were visualized using the Pheatmap package.

Statistical Analysis.

Mean and standard deviation values were calculated using Microsoft Excel software. The treatment effects in each experiment were compared by one-way ANOVA or t-test. Differences between groups were considered significant at $P<0.05$.

All experiments were repeated two to three times. In animal experiments, we used three to four animals/experimental group. In all figures, the results of one representative experiment are shown as mean values±SD.

REFERENCES

1. Adcock I M. Glucocorticoid-regulated transcription factors. Pulm Pharmacol Ther. 2001; 14:211-219.
2. Baida G, Bhalla P, Yuen K, Guo S, Lavker R M, Budunova I. mTOR inhibitor REDD1 protects CD34+ follicular epithelial stem cells and prevents development of steroid-induced cutaneous atrophy. J Invest Dermatol. 2013; 133:S243-S246.
3. Beswick E J, Reyes V E. CD74 in antigen presentation, inflammation, and cancer. World J Gastroenterol. 2009; 15:2855-2861.
4. Boukamp P, Petrussevska R T, Breitkreutz D, Hornung J, Markham A, Fusenig N E. Normal keratinization in a spontaneously immortalized aneuploid human keratinocyte cell line. J Cell Biol. 1988; 106:761-771.
5. Brafman A, Mett I, Shafir M, Gottlieb H, Damari G, Gozlan-Kelner S, Vishnevskia-Dai V, Skaliter R, Einat P, Faerman A, et al Inhibition of oxygen-induced retinopathy in RTP801-deficient mice. Invest Ophthalmol Vis Sci. 2004; 45:3796-3805.
6. Brugarolas J, Lei K, Hurley R L, Manning B D, Reiling J H, Hafen E, Witters L A, Ellisen L W, Kaelin W G., Jr Regulation of mTOR function in response to hypoxia by REDD1 and the TSC1/TSC2 tumor suppressor complex. Genes Dev. 2004; 18:2893-2904.
7. Chebotaev D, Yemelyanov A, Budunova I. The mechanisms of tumor suppressor effect of glucocorticoid receptor in skin. Mol Carcinog. 2007a; 46:732-740.
8. Chebotaev D, Yemelyanov A, Zhu L, Lavker R M, Budunova I. The tumor suppressor effect of the glucocorticoid receptor in skin is mediated via its effect on follicular epithelial stem cells. Oncogene. 2007b; 26:3060-3068.
9. Chebotaev D V, Yemelyanov A, Lavker R M, Budunova I. Epithelial cells in the hair follicle bulge do not contribute to epidermal regeneration after glucocorticoid-induced cutaneous atrophy. J Invest Dermatol. 2007c; 127: 2749-2758.
10. Checkley L A, Rho O, Moore T, Hursting S, DiGiovanni J. Rapamycin is a potent inhibitor of skin tumor promotion by 12-O-tetradecanoylphorbol-13-acetate. Cancer Prev Res. 2011; 4:1011-1020.
11. Clark A R, Martin J R, Tchen C R. Role of dual specificity phosphatases in biological responses to glucocorticoids. J Biol Chem. 2008; 283:25765-25769.
12. Corominas-Faja B, Cuff S, Oliveras-Ferraros C, Cuyàs E, López-Bonet E, Lupu R, Alarcón T, Vellon L, Iglesias J M, Leis O, et al. Nuclear reprogramming of luminal-like breast cancer cells generates Sox2-overexpressing cancer stem-like cellular states harboring transcriptional activation of the mTOR pathway. Cell Cycle. 2013; 12:3109-3124.
13. De Bosscher K, Vanden Berghe W, Haegeman G. The interplay between the glucocorticoid receptor and nuclear factor-kappaB or activator protein-1: molecular mechanisms for gene repression. Endocr Rev. 2003; 24:488-522.
14. De Bosscher K, Haegeman G, Elewaut D. Targeting inflammation using selective glucocorticoid receptor modulators. Curr Opin Pharmacol. 2010; 10:497-504.
15. De Guzman Strong C, Conlan S, Deming C B, Cheng J, Sears K E, Segre J A. A milieu of regulatory elements in the epidermal differentiation complex syntenic block: implications for atopic dermatitis and psoriasis. Hum Mol Genet. 2010; 19:1453-1460.
16. DeYoung M P, Horak P, Sofer A, Sgroi D, Ellisen L W. Hypoxia regulates TSC1/2-mTOR signaling and tumor suppression through REDD1-mediated 14-3-3 shuttling. Genes Dev. 2008; 22:239-251.
17. Driskell R R, Lichtenberger B M, Hoste E, Kretzschmar K, Simons B D, Charalambous M, Ferron S R, Herault Y, Pavlovic G, Ferguson-Smith A C, et al. Distinct fibroblast lineages determine dermal architecture in skin development and repair. Nature. 2013; 504:277-281.
18. Dudley J T, Sirota M, Shenoy M, Pai R K, Roedder S, Chiang A P, Morgan A A, Sarwal M M, Pasricha P J, Butte A J. Computational repositioning of the anticonvulsant topiramate for inflammatory bowel disease. Sci Transl Med. 2011; 3:96-103.
19. Ellisen L W, Ramsayer K D, Johannessen C M, Yang A, Beppu H, Minda K, Oliner J D, McKeon F, Haber D A. REDD1, a developmentally regulated transcriptional target of p63 and p53, links p63 to regulation of reactive oxygen species. Mol Cell. 2002; 10:995-1005.
20. Ellisen L W. Growth control under stress: mTOR regulation through the REDD1-TSC pathway. Cell Cycle. 2005; 4:1500-1502.
21. Engreitz J M, Morgan A A, Dudley J T, Chen R, Thathoo R, Altman R B, Butte A J. Content-based microarray search using differential expression profiles. BMC Bioinformatics. 2010; 11:603-614.
22. Getsios S, Simpson C L, Kojima S, Harmon R, Sheu L J, Dusek R L, Cornwell M, Green K J. Desmoglein 1-dependent suppression of EGFR signaling promotes epidermal differentiation and morphogenesis. J Cell Biol. 2009; 185:1243-1258.
23. Guillou H, Zadravec D, Martin P G, Jacobsson A. The key roles of elongases and desaturases in mammalian fatty acid metabolism: insights from transgenic mice. Prog Lipid Res. 2010; 49:186-199.
24. Henneicke H, Gasparini S J, Brennan-Speranza T C, Zhou H, Seibel M J. Glucocorticoids and bone: local effects and systemic implications. Trends Endocrinol Metab. 2014; 25:197-211.

25. Huang D W, Sherman B T, Lempicki R A. Systematic and integrative analysis of large gene lists using DAVID Bioinformatics Resources. Nat Protoc. 2009a; 4:44-57.
26. Huang D W, Sherman B T, Lempicki R A. Bioinformatics enrichment tools: paths toward the comprehensive functional analysis of large gene lists. Nucleic Acids Res. 2009b; 37:1-13.
27. Imagawa K, Ohkuma S. A case of fat injection for treating subcutaneous atrophy caused by local administration of corticosteroid. Tokai J Exp Clin Med. 2010; 35:66-69.
28. Jablonska S, Groniowska M, Dabroswki J. Comparative evaluation of skin atrophy in man induced by topical corticoids. Br J Dermatol. 1979; 100:193-206.
29. de Jonge H J, Fehrmann R S, de Bont E S, Hofstra R M, Gerbens F, Kamps W A, de Vries E G, van der Zee A G, to Meerman G J, ter Elst A. Evidence based selection of housekeeping genes. PLoS One. 2007; 2:e898.
30. Kamocki K, Van Demark M, Fisher A, Rush N I, Presson R G, Hubbard W, Berdyshev E V, Adamsky S, Feinstein E, Gandjeva A, et al. RTP801 is required for ceramide-induced cell-specific death in the murine lung. Am J Respir Cell Mol Biol. 2013; 48:87-93.
31. Katiyar S, Liu E, Knutzen C A, Lang E S, Lombardo C R, Sankar S, Toth J I, Petroski M D, Ronai Z, Chiang G G. REDD1, an inhibitor of mTOR signalling, is regulated by the CUL4A-DDB1 ubiquitin ligase. EMBO Rep. 2009; 10:866-872.
32. Klionsky D J, Abdalla F C, Abeliovich H, Abraham R T, Acevedo-Arozena A, Adeli K, Agholme L, Agnello M, Agostinis P, Aguirre-Ghiso J A, et al. Guidelines for the use and interpretation of assays for monitoring autophagy. Autophagy. 2012; 8:445-544.
33. Larsen L, Ropke C. Suppressors of cytokine signalling: SOCS. APMIS. 2002; 110:833-844.
34. Lehmann P, Zheng P, Lavker R M, Kligman A M. Corticosteroid atrophy in human skin. A study by light, scanning, and transmission electron microscopy. J Invest Dermatol. 1983; 81:169-176.
35. Li L, Lou Z, Wang L. The role of FKBPS in cancer aetiology and chemoresistance. Br J Cancer. 2011; 104:19-23.
36. Li X H, Ha C T, Fu D, Xiao M. REDD1 protects osteoblast cells from gamma radiation-induced premature senescence. PLoS ONE. 2012; 7:e36604.
37. Lin L, Qian Y, Shi X, Chen Y. Induction of a cell stress response gene RTP801 by DNA damaging agent methyl methanesulfonate through CCAAT/enhancer binding protein. Biochemistry. 2005; 44:3909-3914.
38. Lubach D, Kietzmann M. Investigation of the skin thinning effect of prednicarbate and other corticoids in mouse skin. Skin Pharmacol. 1988; 1:200-206.
39. Mata M A, Satterly N, Versteeg G A, Frantz D, Wei S, Williams N, Schmolke M, Peña-Llopis S, Brugarolas J, Forst C V, et al. Chemical inhibition of RNA viruses reveals REDD1 as a host defense factor. Nat Chem Biol. 2011; 7:712-719.
40. Molitoris J K, McColl K S, Swerdlow S, Matsuyama M, Lam M, Finkel T H, Matsuyama S, Distelhorst C W. Glucocorticoid elevation of dexamethasone-induced gene 2 (Dig2/RTP801/REDD1) protein mediates autophagy in lymphocytes. J Biol Chem. 2011; 286:30181-30189.
41. Necela B M, Cidlowski J A. Mechanisms of glucocorticoid receptor action in noninflammatory and inflammatory cells. Proc Am Thorac Soc. 2004; 1:239-246.
42. Nixon M, Andrew R, Chapman K E. It takes two to tango: dimerisation of glucocorticoid receptor and its anti-inflammatory functions. Steroids. 2013; 78:59-68.
43. Pan J, Ju D, Wang Q, Zhang M, Xia D, Zhang L, Yu H, Cao X. Dexamethasone inhibits the antigen presentation of dendritic cells in MHC class II pathway. Immunol Lett. 2001; 76:153-161.
44. Park K K, Ko D H, You Z, Heiman A S, Lee H J. Synthesis and pharmacological evaluations of new steroidal anti-inflammatory antedrugs: 9alpha-Fluoro-11beta, 17alpha, 21-trihydroxy-3,20-dioxopregna-1,4-diene-16alpha-carboxylate (FP16CM) and its derivatives. Steroids. 2006; 71:83-89.
45. Park K W, Halperin D S, Tontonoz P. Before they were fat: adipocyte progenitors. Cell Metab. 2008; 8:454-457.
46. Pineau P, Volinia S, McJunkin K, Marchio A, Battiston Terris C B, Mazzaferro V, Lowe S W, Croce C M, Dejean A. miR-221 overexpression contributes to liver tumorigenesis. Proc Natl Acad Sci USA. 2010; 107:264-269.
47. Ratman D, Vanden Berghe W, Dejager L, Libert C, Tavernier J, Beck I M, De Bosscher K. How glucocorticoid receptors modulate the activity of other transcription factors: a scope beyond tethering. Mol Cell Endocrinol. 2013; 380:41-54.
48. Regazzetti C, Dumas K, Le Y, Marchand-Brustel F, Peraldi P, Tanti J F, Giorgetti-Peraldi S. Regulated in Development and DNA Damage Responses-1 (REDD1) protein contributes to insulin signaling pathway in adipocytes. PLoS ONE. 2012; 7:e52154.
49. Schäcke H, Schottelius A, Dicke W D, Strehlke P, Jaroch S, Schmees N, Rehwinkel H, Hennekes H, Asadullah K. Dissociation of transactivation from transrepression by a selective glucocorticoid receptor agonist leads to separation of therapeutic effects from side effects. Proc Natl Acad Sci USA. 2004; 101:227-232.
50. Schäcke H, Rehwinkel H, Asadullah K, Cato A C. Insight into the molecular mechanisms of glucocorticoid receptor action promotes identification of novel ligands with an improved therapeutic index. Exp Dermatol. 2006; 15:565-573.
51. Schäcke H, Zollner T M, Döcke W D, Rehwinkel H, Jaroch S, Skuballa W, Neuhaus R, May E, Zügel U, Asadullah K. Characterization of ZK 245186, a novel, selective glucocorticoid receptor agonist for the topical treatment of inflammatory skin diseases. Br J Pharmacol. 2009; 158:1088-1103.
52. Schoepe S, Schäcke H, May E, Asadullah K. Glucocorticoid therapy-induced skin atrophy. Exp Dermatol. 2006; 15:406-420.
53. Schoepe S, Schäcke H, Bernd A, Zöller N, Asadullah K. Identification of novel in vitro test systems for the determination of glucocorticoid receptor ligand-induced skin atrophy. Skin Pharmacol Physiol. 2010; 23:139-151.
54. Sheehan D C, Hrapchak B. Theory and Practice of Histotechnology. St Louis, Mo., USA: The C.V. Mosby Company; 1980.
55. Shimizu N, Yoshikawa N, Ito N, Maruyama T, Suzuki Y, Takeda S, Nakae J, Tagata Y, Nishitani S, Takehana K, et al. Crosstalk between glucocorticoid receptor and nutritional sensor mTOR in skeletal muscle. Cell Metab. 2011; 13:170-182.
56. Shoshani T, Faerman A, Mett I, Zelin E, Tenne T, Gorodin S, Moshel Y, Elbaz S, Budanov A, Chajut A, et al. Identification of a novel hypoxia-inducible factor 1-responsive gene, RTP801, involved in apoptosis. Mol Cell Biol. 2002; 22:2283-2293.

57. Smyth G K. Limma: linear models for microarray data. In: Gentleman R, Carey V, Dudoit S, Irizarry R, Huber W, et al., editors. Bioinformatics and Computational Biology Solutions using R and Bioconductor. New York: Springer; 2005. pp. 397-420.
58. Sofer A, Lei K, Johannessen C M, Ellisen L W. Regulation of mTOR and cell growth in response to energy stress by REDD1. Mol Cell Biol. 2005; 25:5834-5845.
59. Taheri A, Cantrell J, Feldman S R. Tachyphylaxis to topical glucocorticoids; what is the evidence? Dermatol Online J. 2013; 9:18954-18961.
60. Vandevyver S, Dejager L, Libert C. On the trail of the glucocorticoid receptor: into the nucleus and back. Traffic. 2012; 13:364-374.
61. Wang H, Kubica N, Ellisen L W, Jefferson L S, Kimball S R. Dexamethasone represses signaling through the mammalian target of rapamycin in muscle cells by enhancing expression of REDD1. J Biol Chem. 2006; 281:39128-39134.
62. Woodbury R, Kligman A M. The hairless mouse model for assaying the atrophogenicity of topical corticosteroids. Acta Derm Venereol. 1992; 72:403-406.
63. Wu W, Chaudhuri S, Brickley D R, Pang D, Karrison T, Conzen S D. Microarray analysis reveals glucocorticoid-regulated survival genes that are associated with inhibition of apoptosis in breast epithelial cells. Cancer Res. 2004; 64:1757-1764.
64. Yemelyanov A, Czwornog J, Chebotaev D, Karseladze A, Kulevitch E, Yang X, Budunova I. Tumor suppressor activity of glucocorticoid receptor in the prostate. Oncogene. 2007; 26:1885-1896.
65. Yemelyanov A, Czwornog J, Gera L, Joshi S, Chatterton R T, Jr, Budunova I. Novel steroid receptor phyto-modulator compound A inhibits growth and survival of prostate cancer cells. Cancer Res. 2008; 68:4763-4773.
66. Yoshida T, Mett I, Bhunia A K, Bowman J, Perez M, Zhang L, Gandjeva A, Zhen L, Chukwuek U, Mao T, et al. Rtp801, a suppressor of mTOR signaling, is an essential mediator of cigarette smoke-induced pulmonary injury and emphysema. Nat Med. 2010; 16:767-773.
67. Zheng P S, Lavker R M, Lehmann P, Kligma A M. Morphologic investigations on the rebound phenomenon after corticosteroid-induced atrophy in human skin. J Invest Dermatol. 1984; 82:345-352.
68. Zufferey R, Dull T, Mandel R J, Bukovsky A, Quiroz D, Naldini L, Trono D. Self-inactivating lentiviral vector for safe and efficient in vivo gene delivery. J Virol. 1998; 72:9873-9880.

Example 6

Use of REDD1 Inhibitors (Regulated in Development and DNA Damage Response 1) to Dissociate Therapeutic and Adverse Atrophogenic Effects of Steroids It is well accepted that GR transrepression plays an important role in anti-inflammatory effects of glucocorticoids, and many metabolic side effects of steroids related to the maintenance of the HPA axis, glucose metabolism and osteoporosis depend on GR homodimer binding to DNA and transactivation (Schäcke et al., 2006; Schäcke et al., 2009; De Bosscher et al., 2010). Thus, our findings here suggest that inhibition of REDD1 modifies function of the GR, shifting glucocorticoid activity towards therapeutic effects, and diminishing their atrophogenic and possibly other metabolic effects.

In collaboration with Dr. Dudley (Mount Sinai School of Medicine, New York), we employed an integrative chemogenomics approach that builds on his previous work developing and applying novel approaches for systematic drug repurposing. Dr. Dudley previously developed methods to collect, aggregate, and integrate molecular drug signatures from the public data, and to query across these data to identify therapeutic patterns of drug effects. Dr. Dudley has developed Integrated Chemogenomic Knowledge Base (ICKB) (Dudley et al., manuscript is in revision) that contains transcriptional signatures (treated vs. control) for more than 2,000 small molecule compounds (70% FDA approved; 30% investigational). We screened ICKB compounds according to their ability to suppress REDD1 transcription, and found several drugs that have a high probability to act as REDD1 inhibitors in vivo (Table 5 below).

In conclusion, we discovered that REDD1 induction plays a causative role in glucocorticoid-induced skin atrophy. Further, our results suggest the clinical relevance of REDD1 as a modifier of GR function and a molecular target for combinational safer GR-targeted therapies in skin and other organs. We predict that REDD1 inhibition by pharmacological inhibitors listed in Table 5 would reduce steroid-induced skin atrophy, and that the combination of glucocorticoids with REDD1 inhibitors could be a new strategy for development of safer topical glucocorticoid treatment regimens in dermatology as well as for a safer systemic treatment with glucocorticoids.

TABLE 5

Potential REDD1 inhibitors among FDA-approved drugs.

| Compound | Description |
| --- | --- |
| levamisole | Antihelminthic with immunomodulatory properties. Used off-label for collagen vascular diseases, and inflammatory skin conditions |
| clofazimine | Antituberculous drug with known immunomodulatory effects. Known to cause reversible hyperpigmentation |
| metronidazole | Anerobic antimicrobial used in dermatology for rosacea |
| bucladesine | cAMP analogue previously investigated for applications in impaired wound healing and inflammatory skin conditions |
| tenoxicam | NSAID available as a topical formulation |
| physostigmine | Reversible cholinesterase inhibitor |

Example 7

Figure 11:
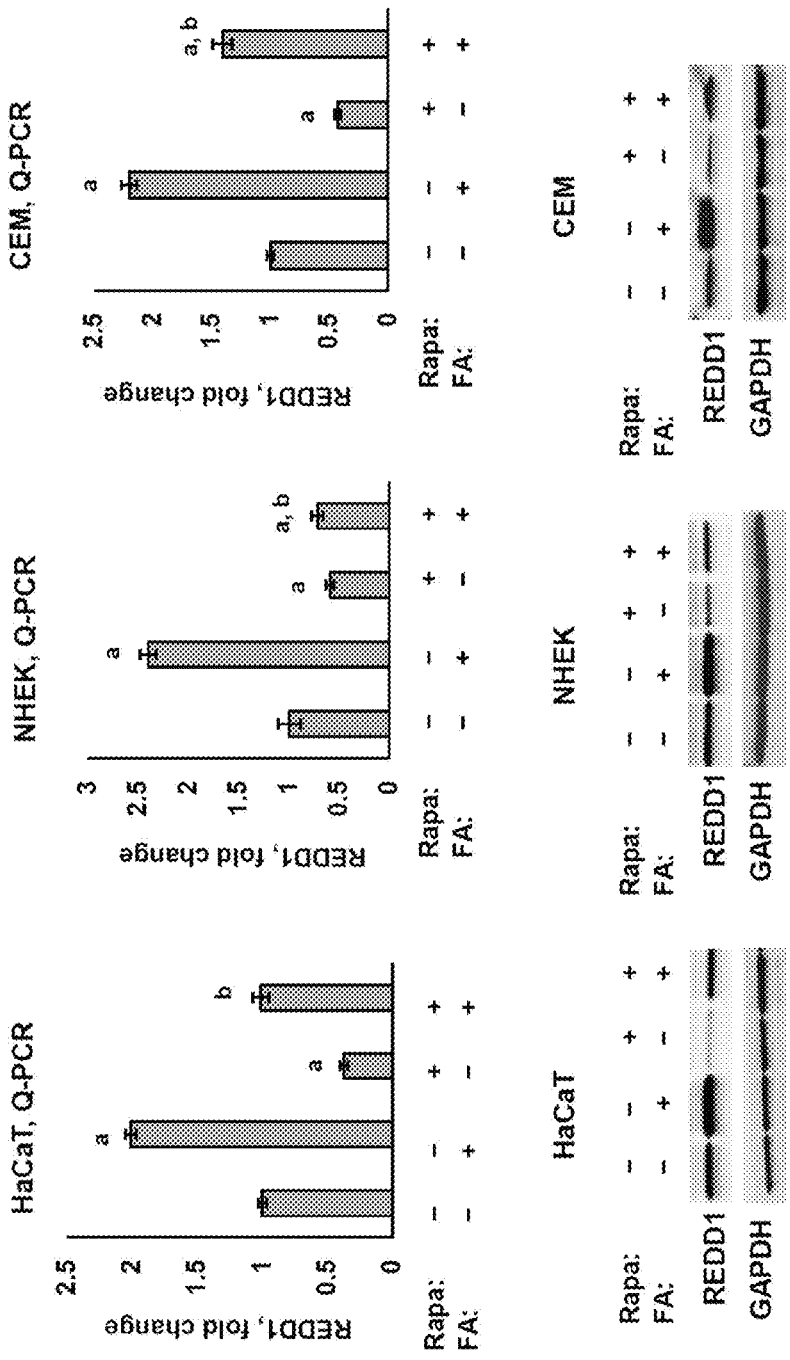
FIG. 11. Rapamycin inhibits REDD1 expression in keratinocytes and lymphoid cells. HaCaT immortalized keratinocytes, NHEK primary human keratinocytes and lymphoid CEM cells were pretreated with Rapa (1 uM×6 hrs) and treated with solvent (Control) or FA (1 uM) for 24 h. A. Q-PCR analysis of REDD1 expression. The results were normalized to the expression of the housekeeping Rp127 gene, and presented as fold of change compared to control cells. The means+/−SD calculated for three individual RNA samples/condition. a—Statistically significant difference (P<0.05) compared to control; b—Statistically significant differences (P<0.05) compared to FA treatment. B. Western blot analysis of REDD1 in whole cell protein extracts. Membranes were probed with anti-GAPDH antibodies to verify equal protein loading and transfer.

Use of Rapamycin to Reduce Expression of REDD1 and Protect Against Skin Atrophy Induced by Glucocorticoid FA Reference is made to the results presented in FIGS. 11-17. The results presented in FIG. 11 demonstrate that rapamycin inhibits REDD1 mRNA and protein expression. The prediction that pharmacological mTOR inhibitor Rapamycin will reduce the expression of genetic mTOR inhibitor, REDD1, was unexpected. We tested whether Rapamycin could indeed cause a down-regulation of REDD1 using different cell types including keratinocytes (immortalized non-transformed human keratinocyte cell line HaCaT and primary human epidermal keratinocytes, NHEK). We also used lymphoid cells (transformed T-cells, CEM) as glucocorticoid effects in lymphocytes are critically important for anti-inflammatory activity of these steroids. The Rapamycin treatment outcomes were remarkably similar in all cells under study: it inhibited both basal and FA-induced REDD1 at mRNA and protein levels (FIG. 11).

Figure 12:
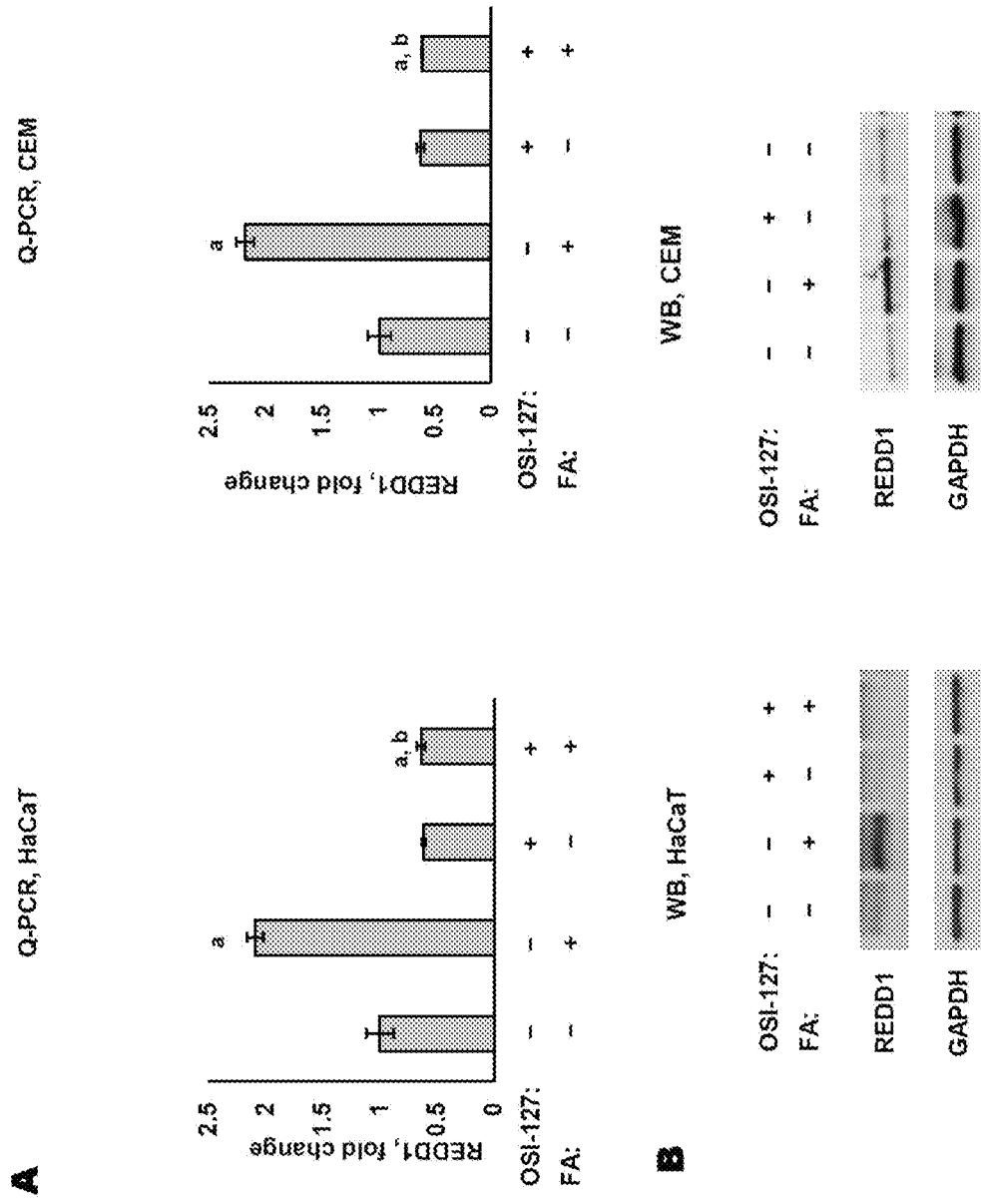
FIG. 12. Pan-inhibitor of mTOR, OSI-127, down-regulates REDD1 expression in keratinocytes and lymphoid cells. HaCaT keratinocytes and CEM lymphoid cells were pretreated with OSI-127 (1 uM×6 h) and then treated with solvent (Control) or FA for (1 uM) for 24 h. A. Q-PCR analysis of REDD1 expression in HaCaT and CEM cells. The results were normalized to the expression of the housekeeping Rp127 gene, and presented as fold of change compared to control cells. The means+/−SD calculated for three individual RNA samples/condition. a—Statistically significant difference (P<0.05) compared to control; b—Statistically significant differences (P<0.05) compared to FA treatment. B. Western blot analysis of REDD1 in whole cell protein extracts. Membranes were probed with anti-GAPDH antibodies to verify equal protein loading and transfer.

The results presented in FIG. 12 demonstrate that a dual inhibitor of mTORC1/mTORC2, OSI-027, also down-regulates REDD1 expression. There are two branches of mTOR signaling mediated by distinct complexes, mTOR complexes 1 (mTORC1) and 2 (mTORC2). Rapamycin is the specific inhibitor of mTORC1, and does not affect mTORC2 (Colamonici et al., 2015; Carayol et al., 2010). To test whether dual mTOR targeting would also result in REDD1 inhibition, we used OSI-027, one of the newly developed catalytic mTORC1/mTORC2 inhibitors, which blocks ATP-binding to both mTOR complexes (Thoreen et al., 2009; Feldman et al., 2009; Bhagwat et al., 2011). We employed the same 6 hr pre-treatment regiment as for Rapamycin, and demonstrated that OSI-127 (1-5 uM) potently inhibited both basal and glucocorticoid-induced REDD1 mRNA and protein in HaCaT keratinocytes and lymphoid CEM cells (FIGS. 12A, B, and data not shown).

Figure 13:
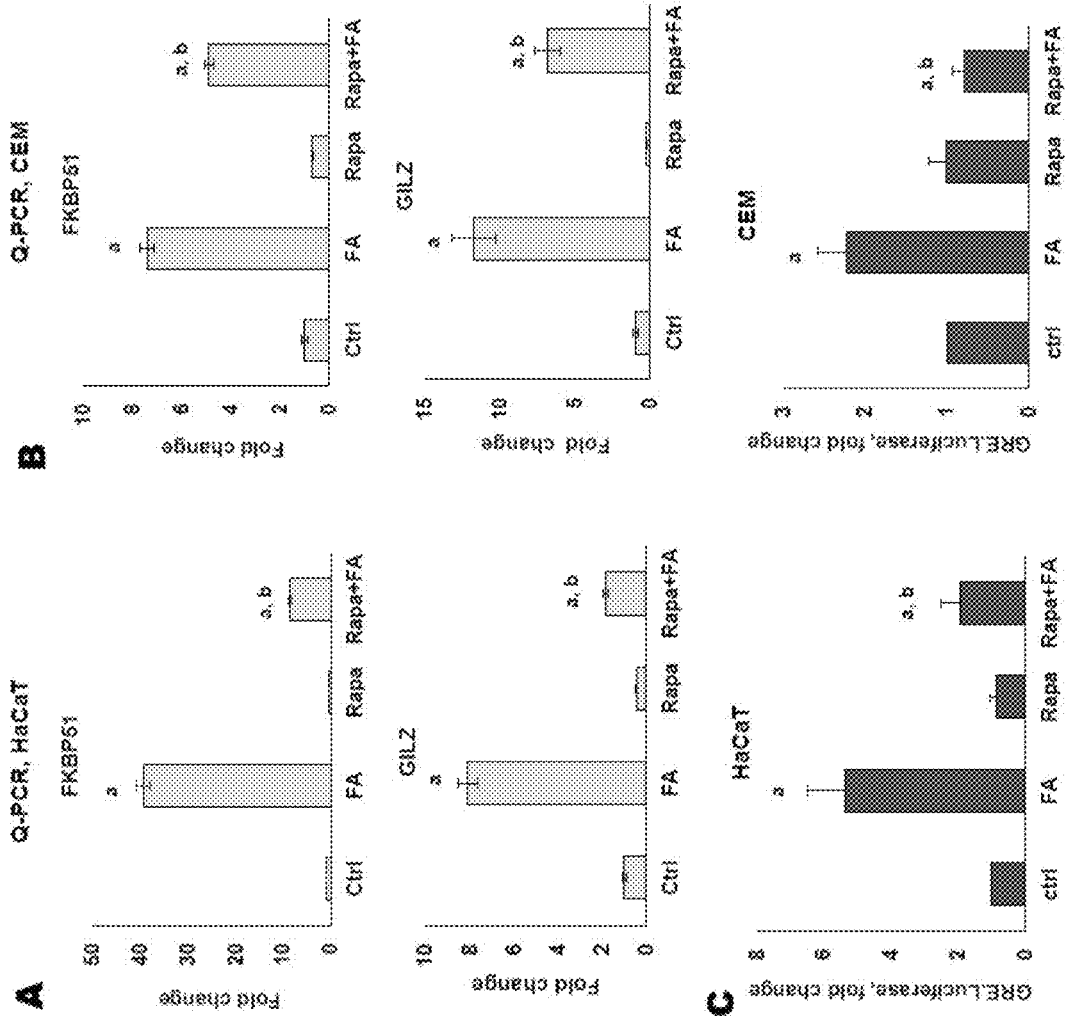
FIG. 13. Rapamycin inhibits GR transactivation. A, B. Q-PCR analysis of FKBP51 and GILZ expression in HaCaT (A) and CEM (B) cells. Cells were pretreated with solvent or Rapa (1 uM)×6 hrs and treated with solvent (Control) or FA (1 uM) for 24 h. A,B. Q-PCR results were normalized to the expression of the housekeeping Rp127 gene, and presented as fold of change compared to control cells. The means+/−SD calculated for three individual RNA samples/condition. a—Statistically significant difference (P<0.05) compared to control; b—Statistically significant differences (P<0.05) compared to FA treatment. C. Inhibitory effect of rapamycin on GRE.Luciferase reporter. HaCaT and CEM cells stably infected with lentivirus expressing GRE.Luciferase reporter were pretreated with 1 uM Rapa for 6 h and then treated with solvent (Control) or FA (1 uM) for 8 hr. The Luciferase induction is presented as a fold change to corresponding vehicle-treated control. The means+SD were calculated for three individual wells/group in one representative experiment (out of three experiments). a—Statistically significant differences (P<0.05) in comparison to vehicle treatment; b—Statistically significant differences (P<0.05) in comparison to FA treatment.
Figure 14:
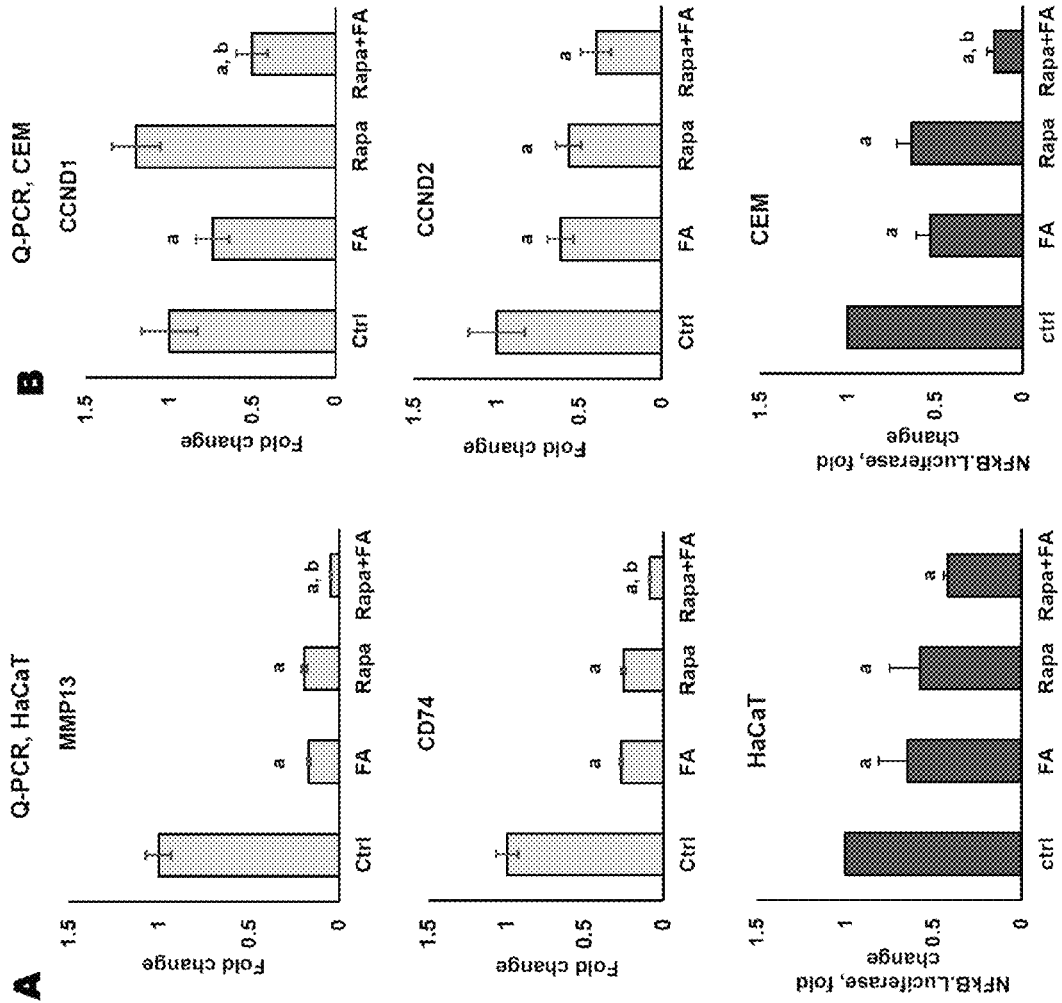
FIG. 14. Rapamycin enhances GR transrepression. A, B. Q-PCR analysis of MMP13 and CD74 expression in HaCaT cells (A) and cyclin D1 (CCND1) and cyclin D2 (CCND2) expression in CEM cells (B). Cells were pretreated with solvent or Rapa (1 uM)×6 hrs and treated with solvent (Control) or FA (1 uM) for 24 h. A, B. Q-PCR results were normalized to the expression of the housekeeping Rp127 gene, and presented as fold of change compared to control cells. The means+/−SD calculated for three individual RNA samples/condition. a—Statistically significant difference (P<0.05) compared to control; b—Statistically significant differences (P<0.05) compared to FA treatment. C. Effect of rapamycin on kappaB.Luciferase reporter. HaCaT and CEM cells stably infected with lentivirus expressing kappaB.Luciferase reporter were pretreated with 1 uM Rapa for 6 h and then treated with solvent (Control) or FA (1 uM) for 8 hr. The Luciferase induction is presented as a fold change to corresponding vehicle-treated control. The means+SD were calculated for three individual wells/group in one representative experiment (out of three experiments). a—Statistically significant differences (P<0.05) in comparison to vehicle treatment; b—Statistically significant differences (P<0.05) in comparison to FA treatment.

The results presented in FIG. 13 and FIG. 14 demonstrate that rapamycin modifies GR function and shifts its activity towards transrepression. GR regulates the expression of numerous genes via different mechanisms including DNA-binding dependent TA. To test whether negative effect of Rapamycin on transcription activation by glucocorticoids was a more general phenomenon, and not only REDD1-specific, we assessed activation of other endogenous GR target genes such as GR chaperone immunophilin FKBP51 and glucocorticoid-induced leucine zipper GILZ, as well as activation of GRE.Luciferase reporter in the presence of Rapamycin. As shown by the results presented in FIG. 13, FA strongly activated FKBP51 and GILZ in HaCaT keratinocytes and CEM lymphoid cells (FIGS. 13A, B). Pre-treatment with Rapamycin robustly inhibited FA-induced expression of these GR-target genes (FIGS. 13A, B). In our next experiments, we used Luciferase assay in keratinocytes and lymphocytes stably infected with lentivirus expressing GRE.Luciferase reporter, and confirmed that Rapamycin impeded GR transcriptional activation by glucocorticoid (FIG. 13C). We also observed a modest negative Rapamycin effect on the basal level of expression of these GR-dependent genes (FIG. 13C).

As shown by the results presented in FIG. 14, the gene repression by glucocorticoids in many instances is mediated via negative interaction between GR and other transcription factors, including NF-kB, followed by down-regulation of their target pro-proliferative and pro-inflammatory genes from interleukin, interferon, matrix metalloproteinase (MMP), cyclin and other families. GR transcriptional signature strongly depends on the cell type. Thus, we focused on the genes that were according to our previous work specifically down-regulated by glucocorticoids in keratinocytes and lymphoid cells. Both, FA and Rapamycin in single treatments inhibited NF-kB activity in Luciferase test, and the basal expression of NF-kB dependent genes cyclins D1 and D2, MMP1 and CD74 (the last one is a regulator of antigen presentation and immune response) (FIG. 14) Importantly, we observed additive/synergistic inhibitory effect of FA and Rapamycin on NF-kB activity (FIG. 14C) and NF-kB-dependent gene expression (FIG. 14A), especially in HaCaT keratinocytes.

Figure 15:
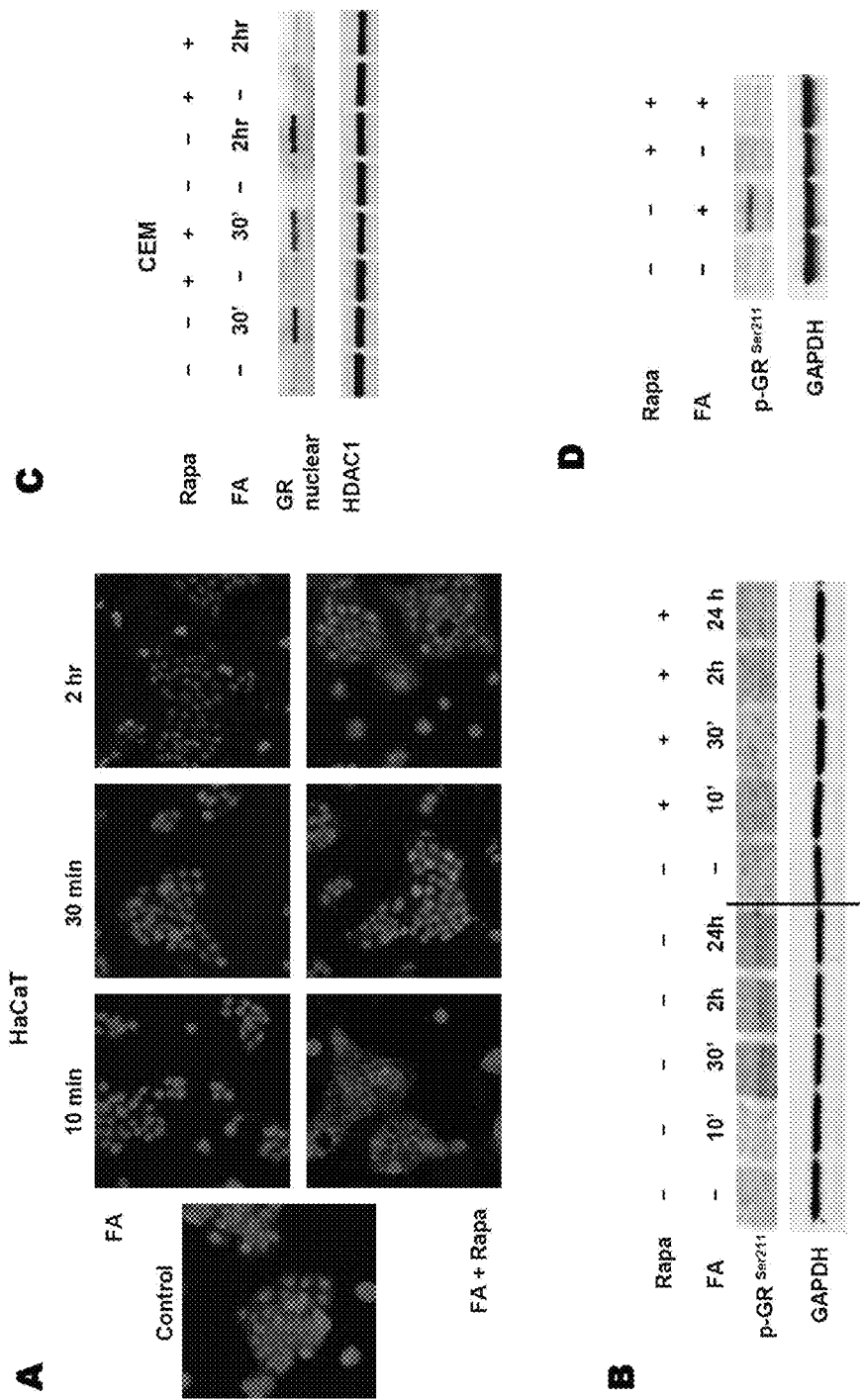
FIG. 15. Rapamycin inhibits GR nuclear translocation and phosphorylation. A. GR nuclear translocation in HaCaT cells was determined by immunofluorescence as described in Materials and Methods. Cells on coverslips were pretreated with solvent (Control) or Rapamycin (1 uM×6 h) and treated with 1 uM FA for indicated time. B. GR nuclear translocation in CEM cells was determined by Western blot analysis of nuclear protein extracts. Membranes were probed with anti-HDAC-1 antibodies to verify equal protein loading and transfer. C, D. GR phosphorylation in HaCaT (C) and CEM (D) cells was determined by Western blot analysis of whole cell lysates. Membranes were probed with anti-GAPDH antibodies to verify equal protein loading and transfer.

The results in FIG. 15 demonstrate that rapamycin inhibits GR nuclear translocation and phosphorylation. To understand the mechanisms of modulatory effect of rapamycin on GR functions, we evaluated its effect on the major steps in GR activation: phosphorylation and nuclear translocation. We assessed GR nuclear translocation by direct immunofluorescence (HaCaT cells) or by Western blot analysis of GR amount in the nuclear protein fractions (CEM cells). In HaCaT cells FA stimulated GR nuclear import in 10 min, and GR remained in the nucleus for 2-24 hrs (FIG. 15A and data not shown). In CEM GR nuclear localization was observed 30 min-2 hrs after FA application (FIG. 15C). Rapamycin pretreatment delayed GR nuclear translocation and accelerated GR export from the nucleus in both CEM and HaCaT cells (FIGS. 15A, C). Further, FA induced quick GR phosphorylation at Ser211 critical for activation of Gcs-responsive genes. GR phosphorylation was almost completely abolished by Rapamycin in both keratinocytes and lymphoid CEM cells, even though the kinetics of these effects was cell type-specific (FIGS. 15B, D).

Figure 16:
FIG. 16. Rapamycin prevents REDD1 activation by glucocorticoids in vivo and does not affect anti-inflammatory effect of glucocorticoids. F1 C57Bl×129 mice were treated topically with solvent (control), FA ((2 μg/mouse×8 hrs) or pretreated with Rapamycin (500 nmol/mouse×6 hrs) followed by FA treatment for 8 h. RNA and whole cell proteins were extracted from epidermis isolated as described in Matherials and Methods. A. Q-PCR analysis of REDD1 expression. The results were normalized to the expression of the housekeeping Rp127 gene, and presented as fold of change compared to control animals. The means+/−SD calculated for three individual RNA samples/condition. a—Statistically significant difference (P<0.05) compared to control; b—Statistically significant differences (P<0.05) compared to FA treatment. B. Western blot analysis of whole cell proteins in epidermis. Membranes were probed with anti-GAPDH antibodies to verify equal protein loading and transfer. C. Ear edema test. Ear edema was induced by croton oil (CO, 20 ul/ear) as in Materials and Methods. Solvent (20 ul/ear) or FA (1 ug/ear) were applied 1 h before CO after 6 hrs of pre-treatment with rapamycin (200 ng/ear) or solvent. Mice were sacrificed and four-millimeter ear punches were weighed 9 h after CO application to assess swelling. Ear punch weight results are presented as % to control (only solvent treatment) ear weight The means+/− SD were calculated for six individual ear punches/condition in one representative experiment (out of three experiments). a—Statistically significant differences (P<0.05) compared to control treatment; b—Statistically significant differences (P<0.05) compared to CO or CO+rapa treatment.
Figure 17:
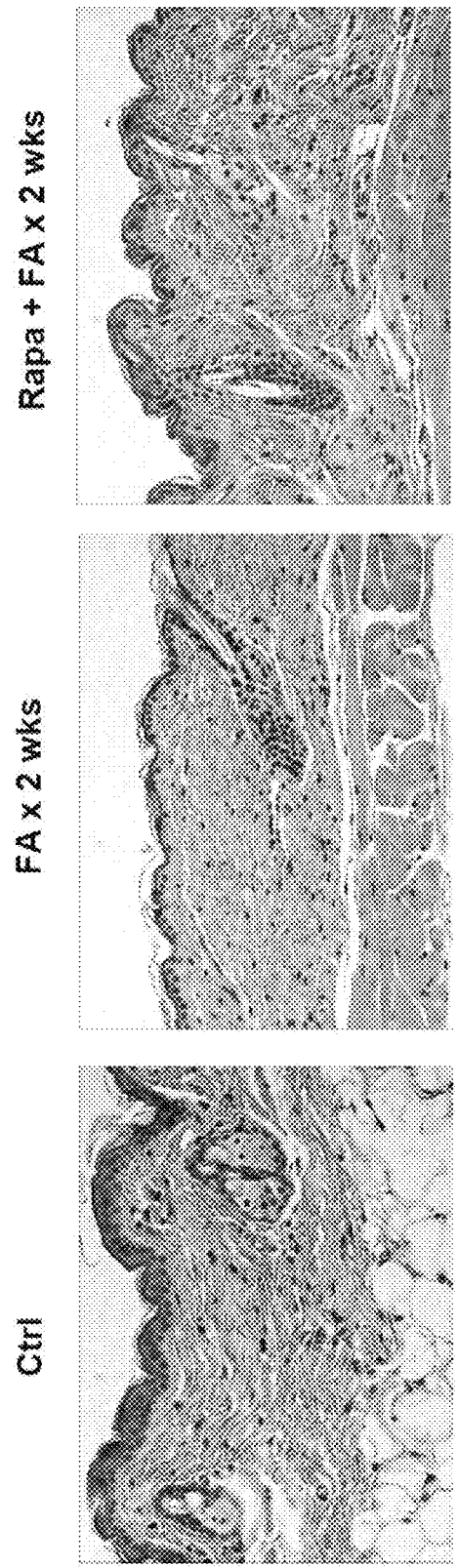
FIG. 17. Rapamycin protects skin against steroid-induced atrophy. Skin atrophy test. B6×129 mice were treated with acetone (vehicle control), FA (2 ug/animal) or pretreated with rapamycin (500 ug/animal×5 hrs) followed by FA. All treatments were done every 72 h for 2 weeks. Skin was harvested, fixed in formalin, H&E staining of skin sections was performed.

The results presented in FIG. 16 and FIG. 17 demonstrate that rapamycin prevents REDD1 activation by glucocorticoids in vivo, protects skin against steroid-induced atrophy and does not affect anti-inflammatory effect of glucocorticoids. In our next set of experiments, we assessed whether Rapamycin prevents REDD1 induction by glucocorticoids in vivo, and whether and how Rapamycin affects therapeutic anti-inflammatory and atrophogenic effects of topical glucocorticoids in skin. As shown by the results in FIG. 16, we treated F1 C57B1×129 mice topically with FA (2 ug/animal×24 h). In good correlation with our previous results (Baida et al., 2015), FA strongly induced REDD1 expression in skin and induced severe skin atrophy after 2 wk treatment (FIG. 16). The pre-treatment of animals with rapamycin which was applied topically in solvent (70% EtOH) to the back skin, drastically blocked REDD1 induction in epidermis by FA both at mRNA and protein levels (FIG. 16A). Thus rapamycin has similar negative effects on REDD1 in keratinocytes in vitro and in vivo. To assess whether Rapamycin affects therapeutic effect of glucocorticoid FA, we used croton oil-induced ear edema test. As expected, croton oil induced inflammation in mouse ears resulting in 2.5-fold weight increase and glucocorticoid FA reduced edema decreasing the ear weight to control level (FIG. 16C). Rapamycin did not affect either edema induction, or FA antinflammatory effect in this test (FIG. 16C).

As shown by the results in FIG. 17, remarkably, rapamycin significantly reduced steroid epidermal atrophy: in mice treated with FA only epidermal thickness was reduced by 50%, compared to ~25% in mice treated with FA+rapamycin (FIG. 17). Interestingly, s.c, adipose tissue was not significantly protected from the atrophy upon Rapamycin treatments (FIG. 17), possibly due to the limited penetration deeper through the skin barrier when applied in solvent (70% EtOH).

REFERENCES

Baida et al., "REDD1 functions at the crossroads between the therapeutic and adverse effects of topical glucocorticoids," EMBO Molec. Med. (2015) 7:42-58

Bhagwat et al., "Preclinical characterization of OSI-027, a potent and selective inhibitor of mTORC1 and mTORC2: distinct from rapamycin," Mol Cancer Ther. 2011 August; 10(8):1394-406.

Carayol et al., "Critical roles for mTORC2- and rapamycin-insensitive mTORC1-complexes in growth and survival of BCR-ABL-expressing leukemic cells," Proc Natl Acad Sci USA 2010 Jul. 13; 107(28):12469-74.

Colamonici et al., "Dual targeting of acute myeloid leukemia progenitors by catalytic mTOR inhibition and blockade of the p100alpha subunit of PI3 kinase," Oncotarget. 2015 Apr. 10; 6(10):8062-70

Feldman et al., "Active-site inhibitors of mTOR target rapamycin-resistant outputs of mTORC1 and mTORC2," PLoS Biol. 2009 Feb. 10; 7(2)e28.

Thoreen et al., "An ATP-competitive mammalian target of rapamycin inhibitor reveals rapamycin-resistant functions of TORC1," J. Biol. Chem. 2009, Mar. 20; 284(12):8023-32.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A method for reducing atrophy in a subject undergoing treatment with a glucocorticoid receptor (GR) agonist, the method comprising administering to the subject an inhibitor of regulated in development and DNA damage response protein 1 (REDD1 inhibitor), wherein the REDD1 inhibitor is administered concurrently with the GR agonist and wherein the subject is administered an effective amount of the REDD1 inhibitor for reducing atrophy of epidermis, subcutaneous fat, or muscle.

2. The method of claim 1, wherein the subject has an inflammatory disease or disorder.

3. The method of claim 2, wherein the inflammatory disease is selected from a group consisting of asthma, arthritis, psoriasis, and dermatitis.

4. The method of claim 1, wherein the subject has a cancer.

5. The method of claim 4, wherein the cancer is a blood cancer selected from a group consisting of leukemia and myeloma.

6. The method of claim 1, wherein the GR agonist is selected from the group consisting of cortisone, cortisol, corticosterone, deoxycorticosterone acetate (DOCA), fluticasone propionate, fluocinolone acetonide (FA), GSK9027, prednisone, prednisolone, methylpredinosolone, dexamethasone, betamethasone, triamcinolone, beclometasone, fludrocortisone acetate, mometasone furoate, clobetasol propionate, and pharmaceutically acceptable salts thereof.

7. The method of claim 1, wherein the REDD1 inhibitor is selected from the group consisting of levamisole, clofazimine, metronidazole, bucladesine, tenoxicam, physostigmine, rapamycin, and pharmaceutically acceptable salts thereof.

8. The method of claim 1, wherein the REDD1 inhibitor inhibits expression of REDD1.

9. The method of claim 1, wherein the REDD1 inhibitor inhibits activity of REDD1.

10. A method for reducing atrophy in a subject undergoing treatment with a glucocorticoid receptor (GR) agonist wherein the subject has previously been administered a GR agonist and the subject is exhibiting negative side effects of GR agonist therapy, the method comprising administering to the subject an inhibitor of regulated in development and DNA damage response protein 1 (REDD1 inhibitor), wherein the REDD1 inhibitor is administered concurrently with the GR agonist and wherein the subject is administered an effective amount of the REDD1 inhibitor for reducing atrophy of epidermis, subcutaneous fat, or muscle.

11. The method of claim 1, wherein the subject has an inflammatory disease or disorder.

12. The method of claim 2, wherein the inflammatory disease is selected from a group consisting of asthma, arthritis, psoriasis, and dermatitis.

13. The method of claim 1, wherein the subject has a cancer.

14. The method of claim 4, wherein the cancer is a blood cancer selected from a group consisting of leukemia and myeloma.

15. A method for reducing atrophy in a subject undergoing treatment with a glucocorticoid receptor (GR) agonist wherein the subject has not previously been administered a GR agonist, the method comprising administering to the subject an inhibitor of regulated in development and DNA damage response protein 1 (REDD1 inhibitor), wherein the REDD1 inhibitor is administered concurrently with the GR agonist and wherein the subject is administered an effective amount of the REDD1 inhibitor for reducing atrophy of epidermis, subcutaneous fat, or muscle.

16. The method of claim 1, wherein the subject has an inflammatory disease or disorder.

17. The method of claim 2, wherein the inflammatory disease is selected from a group consisting of asthma, arthritis, psoriasis, and dermatitis.

18. The method of claim 1, wherein the subject has a cancer.

* * * * *